United States Patent
Hsieh et al.

(10) Patent No.: US 12,103,969 B2
(45) Date of Patent: Oct. 1, 2024

(54) ANTI-SIGLEC ANTIBODY, PHARMACEUTICAL COMPOSITION COMPRISING THE SAME, AND USES THEREOF

(71) Applicant: Academia Sinica, Taipei (TW)

(72) Inventors: Shie-Liang Hsieh, Taipei (TW); Tsung-Yu Tsai, Taipei (TW); An-Suei Yang, Emeryville, CA (US); Chung-Ming Yu, Taipei (TW); Cheng-Yuan Peng, Taichung (TW)

(73) Assignee: Academia Sinica, Taipei (TW)

( * ) Notice: Subject to any disclaimer, the term of this patent is extended or adjusted under 35 U.S.C. 154(b) by 819 days.

(21) Appl. No.: 17/266,092

(22) PCT Filed: Sep. 25, 2018

(86) PCT No.: PCT/US2018/052759
§ 371 (c)(1),
(2) Date: Feb. 4, 2021

(87) PCT Pub. No.: WO2020/068058
PCT Pub. Date: Apr. 2, 2020

(65) Prior Publication Data
US 2021/0292413 A1    Sep. 23, 2021

(51) Int. Cl.
| | | |
|---|---|---|
| *C07K 16/28* | (2006.01) |
| *A61P 25/28* | (2006.01) |
| *A61P 31/20* | (2006.01) |
| *A61K 39/00* | (2006.01) |

(52) U.S. Cl.
CPC .......... *C07K 16/2803* (2013.01); *A61P 25/28* (2018.01); *A61P 31/20* (2018.01); *A61K 2039/505* (2013.01); *C07K 2317/56* (2013.01); *C07K 2317/76* (2013.01); *C07K 2317/77* (2013.01)

(58) Field of Classification Search
None
See application file for complete search history.

(56) References Cited

U.S. PATENT DOCUMENTS

2007/0009540 A1*  1/2007  Amphlett ........... A61K 47/6851
                                                    530/391.1

FOREIGN PATENT DOCUMENTS

| WO | WO-2004043344 A2 * | 5/2004 | ......... A61K 39/3955 |
| WO | WO-2011036183 A2 * | 3/2011 | ......... C07K 16/2803 |
| WO | WO-2012074097 A1 * | 6/2012 | ......... C07K 16/2803 |

* cited by examiner

*Primary Examiner* — Zachary S Skelding
*Assistant Examiner* — Brianna K Swartwout
(74) *Attorney, Agent, or Firm* — NZ CARR LAW OFFICE

(57) ABSTRACT

Disclosed herein is a novel monoclonal antibody exhibiting binding affinity to Siglec-3 receptor. According to the embodiment, the monoclonal antibody is capable of reversing HBV-induced immunosuppression. Accordingly, also disclosed herein are the uses thereof in the treatment and/or prophylaxis of hepatitis B virus (HBV) infection.

10 Claims, 14 Drawing Sheets

Specification includes a Sequence Listing.

(A)

(B)

(C)

(A)

(B)

(F)

(G)

(H)

(A)

(B)

(C)

(D)

(E)

(A)

(B)

(A)

(B)

(A)

(B)

(C)

(D)

(E)

(F)

(G)

(H)

(I)

ANTI-SIGLEC ANTIBODY, PHARMACEUTICAL COMPOSITION COMPRISING THE SAME, AND USES THEREOF

CROSS-REFERENCE TO RELATED APPLICATION

This application is a U.S. National Stage Filing under 35 U.S.C. 371 from International Patent Application Serial No. PCT/US2018/052759, entitled "ANTI-SIGLEC ANTIBODY, PHARMACEUTICAL COMPOSITION COMPRISING THE SAME, AND USES THEREOF," filed on Sep. 25, 2018, and published on Apr. 2, 2020, the disclosure of which are incorporated by reference herein in their entireties.

BACKGROUND OF THE INVENTION

1. Field of the Invention

The present disclosure in general relates to the field of treating infection. More particularly, the present disclosure relates to a novel anti-Siglec antibody and the uses thereof in the treatment and/or prophylaxis of hepatitis B virus (HBV) infection.

2. Description of Related Art

HBV is an enveloped, partially double-stranded DNA virus with unusual features similar to retroviruses. In general, HBV replicates through an RNA intermediate and can integrate into the host genome. The unique features of the HBV replication cycle confer a distinct ability of the virus to persist in infected cells. HBV infection leads to a wide spectrum of liver diseases, including acute hepatitis, chronic hepatitis, cirrhosis and hepatocellular carcinoma (HCC). The World Health Organization (WHO) estimates that globally there are 257 million people living with HBV infection, which causes about 887,000 deaths in 2015.

There is no specific treatment for acute hepatitis B (AHB) infection. Therefore, care is aimed at maintaining comfort and adequate nutritional balance, including replacement of fluids lost from vomiting and diarrhea. As to the chronic hepatitis B (CHB) infection, several medicines have been approved by U.S. Food and Drug Administration (FDA), including entecavir (Baraclude), lamivudine (Epivir HBV), adefovir dipivoxil (Hepsera), interferon alpha-2b (Intron A), pegylated interferon (Pegasys), telbivudine (Tyzeka) and tenofovir (Viread). However, in most people, these treatments do not cure HBV infection, but only suppress the replication of the virus. Therefore, most people who start hepatitis B treatment must continue it for life.

In view of the foregoing, there exists in the related art a need for a novel method for efficiently preventing and/or treating HBV infection so as to reduce the incidence of cirrhosis and HCC, and thus improving the long term survival of patients.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to an antibody or a fragment thereof for the treatment or prophylaxis of HBV infection. The antibody comprises a light chain variable (VL) region and a heavy chain variable (VH) region, in which the VL region comprises a first light chain complementarity determining region (CDR-L1), a second light chain CDR (CDR-L2), and a third light chain CDR (CDR-L3); and the VH region comprises a first heavy chain CDR (CDR-H1), a second heavy chain CDR (CDR-H2), and a third heavy chain CDR (CDR-H3).

According to some embodiments of the present disclosure, the CDR-L1 has the amino acid sequence of VYY, the CDR-L2 has the amino acid sequence of ISSAG (SEQ ID NO: 3), and the CDR-L3 has the amino acid sequence of QYFNFP (SEQ ID NO: 4). In these embodiments, the CDR-H1 has the amino acid sequence of NNGW (SEQ ID NO: 5), the CDR-H2 has the amino acid sequence of GIGPYGGSTF (SEQ ID NO: 6), and the CDR-H3 has the amino acid sequence of SRFIGSYSHM (SEQ ID NO: 7).

Preferably, the VL region comprises the amino acid sequence at least 85% identical to SEQ ID NO: 8, and the VH region comprises the amino acid sequence at least 85% identical to SEQ ID NO: 9. In one specific example, the VL region has the amino acid sequence of SEQ ID NO: 8, and the VH region has the amino acid sequence of SEQ ID NO: 9.

It is therefore the second aspect of this disclosure to provide a use of the present antibody according to any of the above-mentioned embodiments for manufacturing a medicament or a pharmaceutical composition for the prophylaxis or treatment of HBV infection. The medicament or the pharmaceutical composition comprises an effective amount of the antibody described above; and a pharmaceutically acceptable carrier.

The antibody of this invention is present at a level of about 0.1% to 99% by weight, based on the total weight of the pharmaceutical composition or medicament. In some embodiments, the antibody of this invention is present at a level of at least 1% by weight, based on the total weight of the pharmaceutical composition or medicament. In certain embodiments, the antibody of this invention is present at a level of at least 5% by weight, based on the total weight of the pharmaceutical composition or medicament. In still other embodiments, the antibody of this invention is present at a level of at least 10% by weight, based on the total weight of the pharmaceutical composition or medicament. In still yet other embodiments, the antibody of this invention is present at a level of at least 25% by weight, based on the total weight of the pharmaceutical composition or medicament.

Another aspect of the present disclosure pertains to a method of preventing or treating HBV infection in a subject. The present method comprises administering to the subject an effective amount of the antibody, pharmaceutical composition or medicament according to any of the above-mentioned aspects and embodiments.

The subject treatable by the present method is a mammal, for example, human, mouse, rat, guinea pig, hamster, monkey, swine, dog, cat, horse, sheep, goat, cow, and rabbit. Preferably, the subject is a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1:
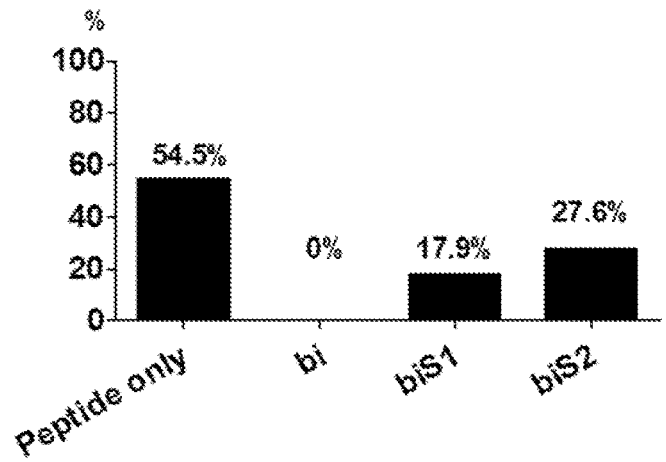
FIG. 1 is the data depicting the percentage of specified glycans on the surface antigen of hepatitis B virus (HBsAg) according to example 1 of the present disclosure. Panel A: the peptide derived from CHB patient-isolated HBV (hHBV) and having the amino acid sequence of SEQ ID NO: 1. Panel B: the peptide derived from hHBV and having the amino acid sequence of SEQ ID NO: 2. Panel C: the peptide derived from transgenic mouse-isolated HBV (mHBV) and having the amino acid sequence of SEQ ID NO: 1. bi: no terminal Neu5Ac; biS1: single Neu5Ac; biS2: two Neu5Ac.

FIG. 2 is the data depicting the interaction of HBV and Siglec-3 according to example 2 of the present disclosure. Panels A and B: immunoprecipitation of hHBV (Panel A) and mHBV (Panel B) by Siglec ECD.Fc fusion proteins. S/M/L: small/middle/large HBsAg, gS: glycosylated small HBsAg. Panel C: determination of hHBV and mHBV interaction with Siglec ECD.Fc by ELISA. Panel D: FRET efficiency between hHBV and Siglec-3,-7,-9 in monocyte-derived dendritic cells (moDC) incubated with hHBV. Panel E: FRET efficiency between hHBV and Siglec-3,-7,-9 in freshly isolated peripheral blood mononuclear cells (PBMCs) of CHB patients (Serum HBV DNA level >2.0×$10^7$ IU/mL). FRET efficiency was determined by FLIM-FRET analyzer software and calculated according to the equation mentioned in "Materials and Methods". Data are expressed as means±s.d. for n=10-15 cells per condition. ** p<0.01 (Student's t-test). Panels F and G: competition assay of hHBV and Siglec-3 interaction by sialoglycan (Panel F) and sialidase-C/sialidase-S treated sialoglycan (Panel G). Panel H: effect of sialidase-C and sialidase-S on hHBV and Siglec-3 interaction. * p<0.05,  p<0.01, * P<0.001 (Student's t-test). All data shown are representative from three independent experiments.

FIG. 3 is the data depicting the suppressive effect of hHBV on TLR ligands-induced cytokine secretion according to example 4 of the present disclosure. Panels A to D: hHBV inhibits cytokine secretion in Pam3csk4-stimulated moDC (Panels A and B) or poly (I:C)-stimulated moDC (Panels C and D). MoDC pretreated with hHBV or mHBV for 24 hours before incubation with pam3csk4 (Panels A and B) or poly(I:C)+interferon-γ (Panels C and D) for another 24 hours. Cytokine levels in the supernatant was determined by ELISA. Data are expressed as means±standard deviation (s.d.) for three independent experiments. * p<0.05,  p<0.01, *: P<0.001 (Student's t-test). Panels E and F: recruitment of SHP-1 and SHP-2 by hHBV in time-dependent (Panel E) and dose-course-dependent manner (Panel F). MoDC was treated with various doses of hHBV (Panel E) or different time (Panel F) to observe recruitment of SHP-1 and SHP-2 in moDC by Western blotting. Signals were quantified by densitometry using software. The value represented the fold change normalized to starting point.

FIG. 4 is the data of specified monoclonal antibodies (mAbs) according to example 5 of the present disclosure. Panel A: association of SHP-1 and SHP-2 with Siglec-3 induced by hHBV or anti-Siglec-3 mAb (clone 2B9 or 10C8) in moDC. Cell lysates were pulled down by anti-Siglec-3 mAb, and SHP-1 and SHP-2 were detected by Western blotting. Panel B: inhibition of TNF-α secretion from pam3csk4-stimulated moDC by anti-Siglec-3 mAb (clone 2B9). MoDC was pretreated with anti-Siglec-3 mAb for 1 hour before incubation with pam3csk4. TNF-α in the supernatant was determined by ELISA. Data are expressed as means±s.d. for three independent experiments.  P<0.01, * P<0.001 (Student's t-test).

FIG. 5 is the data depicting the bio-activity of mAb 10C8 according to example 5.1 of the present disclosure, in which FRET efficiency between Siglec-3 and hHBV was attenuated by Anti-Siglec-3 mAb (clone #10C8). Panel A: the interaction of Siglec-3 and hHBV in PBMC of CHB patients. Panel B: the interaction of Siglec-3 and hHBV in moDC incubated with exogenous hHBV. FRET efficiency was determined by FLIM-FRET analyzer software and calculated according to the equation mentioned in "Materials and Methods". Data are expressed as means±s.d. for n=10-15 cells per condition. ** p<0.01 (Student's t-test).

FIG. 6 is the data depicting the effect of mAb 10C8 on hHBV-mediated immunosuppression according to example 5.2 of the present disclosure. Panels A to D: reversal of cytokine secretion from pam3csk4-stimulated moDC (Panels A and B) or poly (I:C)-stimulated moDC (Panels C and D) by anti-Siglec-3 mAb. MoDC was pretreated with anti-Siglec-3 mAb for 1 hour before incubation with various amounts of hHBV in the presence of pam3csk4 (Panels A and B) or poly (I:C)+IFN-γ (Panels C and D) for 24 hours. Cytokine levels were determined by ELISA. Panel E: inhibition of hHBV-mediated recruitment of SUP-1 and SHP-2 by anti-Siglec-3 mAb. MoDC was pretreated with anti-Siglec-3 mAb for 1 hour before incubation with HBV for 30 minutes, followed by pull down with anti-Siglec-3 mAb. The immunoprecipitates were fractionated on SDS-PAGE before blotting, following by probing with anti-SHP-1 and anti-SuP-2 mAb. Quantification was determined by densitometry using software and the number represented the fold of each value normalized to the value of untreated control. Panels F to I: reversal of cytokine secretion in pam3csk4-stimulated (Panels F and G) and poly (I:C)-stimulated (Panels H and I) PBMC of CHB patients. Freshly isolated PBMCs of CHB patients were pretreated with anti-Siglec-3 mAb followed by incubation with pam3csk4 (Panels F and G) or poly (I.C) (Panels H and I). Cytokine level in the supernatant was analyzed by ELISA. Data are expressed as means±s.d. for three independent experiments. * P<0.05,  p<0.01, * P<0.001.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.
Figure 1:
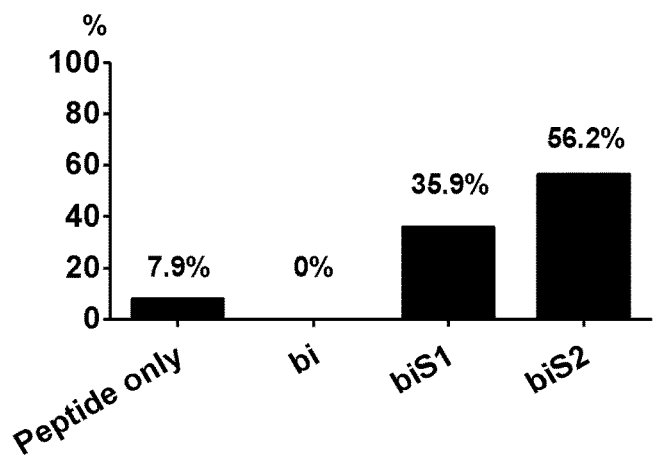
Figure 1:
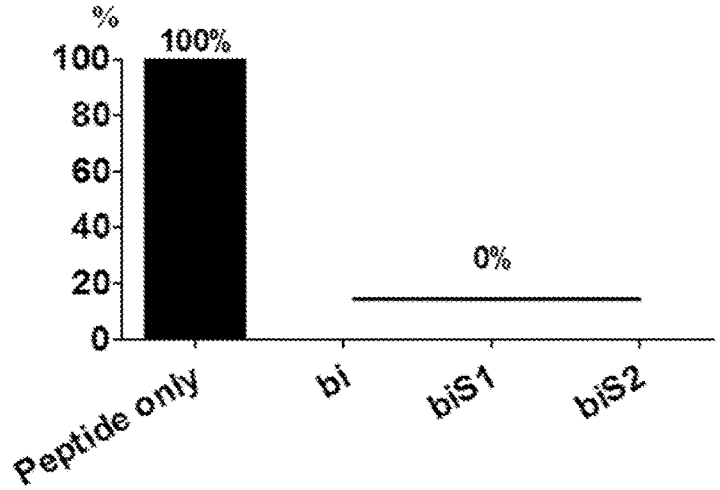

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "antibody" is used in the broadest sense and specifically covers monoclonal antibodies (including full length monoclonal antibodies), polyclonal antibodies, multi-specific antibodies (e.g., bi-specific antibodies), and antibody fragments so long as they exhibit the desired biological activity. "Antibody fragments" comprise a portion of a full length antibody, generally the antigen binding or variable region thereof. Examples of antibody fragments include Fab, Fab', F(ab')2, and Fv fragments; diabodies; linear antibodies; single-chain antibody molecules; and multi-specific antibodies formed from antibody fragments.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment. The antibody fragment in the present invention may exist in a variety of forms including, for example, variable fragment (Fv), single-chain variable fragment (scFv), antigen-binding fragment (Fab) and F(ab)$_2$, as well as single chain antibodies.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

The term "complementarity determining region" (CDR) used herein refers to the hypervariable region of an antibody molecule that forms a surface complementary to the 3-dimensional surface of a bound antigen. Proceeding from N-terminus to C-terminus, each of the antibody heavy and light chains comprises three CDRs (CDR 1, CDR 2, and CDR3). A HLA-DR antigen-binding site, therefore, includes a total of six CDRs that comprise three CDRs from the variable region of a heavy chain and three CDRs from the variable region of a light chain.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

As discussed herein, minor variations in the amino acid sequences of antibodies are contemplated as being encompassed by the presently disclosed and claimed inventive concept(s), providing that the variations in the amino acid sequence maintain at least 85% sequence identity, such as at least 85%, 86%, 87%, 88%, 89%, 90%, 91%, 92%, 93%, 94%, 95%, 96%, 97%, 98% and 99% sequence identity. Antibodies of the present disclosure may be modified specifically to alter a feature of the peptide unrelated to its physiological activity. For example, certain amino acids can be changed and/or deleted without affecting the physiological activity of the antibody in this study (i.e., its ability to treat and/or preventing HBV infection). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of antibodies can be readily prepared by those of ordinary skill in the art. Preferred amino- and carboxyl-termini of fragments or analogs occur near boundaries of functional domains. In one example, one amino acid residue (e.g., valine) of the present antibody is conservatively replaced (e.g., by leucine). In other examples, two amino acid residues of the present antibody are conservatively replaced by other suitable amino acid residues, for example, valine (V) and arginine (R) are replaced by the pair of amino acids that includes, but is not limited to, methionine (M) and lysine (K), lysine (K) and proline (P), tryptophan (W) and isoleucine (I), isoleucine (I) and proline (P), asparagine (N) and valine (V), and glutamine (G) and lysine (K).

"Percentage (%) sequence identity" is defined as the percentage of amino acid residues in a candidate sequence that are identical with the amino acid residues in the specific peptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100$$

where X is the number of amino acid residues scored as identical matches by the sequence alignment program BLAST in that program's alignment of A and B, and where Y is the total number of amino acid residues in A or B, whichever is shorter.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the present antibody), such as molar concentration, mass concentration, volume concentration, molality, mole fraction, mass fraction and mixing ratio. Persons having ordinary skills could calculate the human equivalent dose (HED) for the medicament (such as the present antibody) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

As used herein, the term "treat," "treating" and "treatment" are interchangeable, and encompasses partially or completely preventing, ameliorating, mitigating and/or managing a symptom, a secondary disorder or a condition associated with HBV infection. The term "treating" as used herein refers to application or administration of one or more antibodies of the present disclosure to a subject, who has a symptom, a secondary disorder or a condition associated with HBV infection, with the purpose to partially or completely alleviate, ameliorate, relieve, delay onset of, inhibit progression of, reduce severity of, and/or reduce incidence of one or more symptoms, secondary disorders or features associated with HBV infection. Symptoms, secondary disorders, and/or conditions associated with HBV infection include, but are not limited to, fatigue, nausea, vomiting, dark urine, joint and muscle pain, loss of appetite, fever, abdominal discomfort, weakness, jaundice, and liver failure. Treatment may be administered to a subject who exhibits only early signs of such symptoms, disorder, and/or condition for the purpose of decreasing the risk of developing the symptoms, secondary disorders, and/or conditions associated with HBV infection. Treatment is generally "effective" if one or more symptoms or clinical markers are reduced as that term is defined herein. Alternatively, a treatment is "effective" if the progression of a symptom, disorder or condition is reduced or halted.

The term "prevent," "preventing" and "prophylaxis" as used herein are interchangeable, and refers to the prophylactic treatment of a subject who is at risk of developing a symptom, a secondary disorder or a condition associated with HBV infection, so as to decrease the probability that the subject will develop the symptom, secondary disorder or condition. Specifically, the term "prevent," "preventing" or "prophylaxis" refers to inhibit the occurrence of a symptom, a secondary disorder or a condition associated with HBV infection, that is to reduce the incidence or the frequency of occurrence of the symptom, secondary disorder or condition.

The term "prevent," "preventing" or "prophylaxis" as used herein referring to an antibody, a pharmaceutical composition comprising the same and/or a method, does not mean or imply that use of the antibody, the pharmaceutical composition comprising the same and/or the method will provide a guarantee that the symptom, secondary disorder or condition will never occur, but rather that the antibody, the pharmaceutical composition comprising the same and/or the method will inhibit the occurrence of the symptom, secondary disorder or condition, and that the incidence and/or frequency of the symptom, secondary disorder or condition will be reduced.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "subject" refers to a mammal including the human species that is treatable with methods of the present invention. The term "subject" is intended to refer to both the male and female gender unless one gender is specifically indicated.

II. Description of The Invention

The present disclosure is based, at least in part, on the discovery that HBV exhibits binding affinity to the sialic acid-binding immunoglobulin-like lectin-3 (Siglec-3), and the antibody specific to Siglec-3 is capable of reversing HBV-induced immunosuppression.

Accordingly, the present disclosure provides a monoclonal antibody (mAb) or a fragment thereof, which exhibits binding specificity to Siglec-3 receptor.

According to the embodiments of the present disclosure, the present mAb is produced by phage-displayed scFv libraries. As would be appreciated, the present mAb may alternatively be produced by conventional immunization method (i.e., immunizing animals with specific peptides).

In general, the polypeptide (i.e., Siglec-3 polypeptide) can be synthesized by commonly used methods such as t-BOC or FMOC protection of alpha-amino groups. Both methods involve stepwise syntheses whereby a single amino acid is added at each step starting from the C terminus of the peptide. Polypeptides of the invention can also be synthesized by the well-known solid phase peptide synthesis methods.

Then, the antibody can be produced by immunizing a host animal, such as a mouse, a rat, or a rabbit, with the synthetic polypeptide. The immunization may be performed in accordance with commonly adopted procedures. The immunization interval is not particularly limited. Immunization may be carried out at intervals of several days to several weeks, preferably one week, for 2-10 times, until a desired antibody titer is reached. For example, the host animals may be vaccinated by subcutaneously injecting with the synthetic polypeptide on weekly basis for 8 consecutive weeks.

After the final immunization, splenic cells and regional lymph nodes are removed. Blood samples are taken regularly after immunization and subject to centrifugation to separate sera. The resultant sera are then subject to measurement of antibody titers by any suitable method, which includes, but is not limited to, enzyme linked immunosorbent assay (ELISA), enzyme immunoassay (EIA), or radio immunoassay (RIA). In one preferred example, antibody titers are measured by ELISA. Then, final immunization is given to those animals showing high antibody titers to the synthetic polypeptide. Antibody-producing cells are prepared from splenic cells and regional lymph nodes or the like of the immunized animals. In the preparation of antibody-producing cells, it is preferably to remove tissue debris and erythrocytes as much as possible. Commercial erythrocyte remover may be used to this purpose. Alternatively, a buffer ammonium chloride and Tris may be prepared and used. The thus prepared antibody-producing cells should be immediately fused with immortal cells such as myeloma cells to produce hybridoma cells, which semi-eternally continue to proliferate while producing antibodies. Commonly available cell strain derived from an animal such as mouse may be used. A preferable cell strain to be used in this invention should not survive in HAT selection medium, which contains hypoxanthine, thymidine and aminopterin; and should survive there only when fused with antibody-producing cells. Examples of myeloma cells include, but are not limited to, mouse myeloma cell line (such as myeloma FO cells) and human myeloma cell line (such as Karpas 707H). Cell fusion is usually carried out by mixing splenic cells or lymph node cells with a commercial available myeloma cells in the presence of a cell-fusion promoter, such as polyethylene glycol (PEG) having an average molecular weight from about 200 to 20,000 daltons or the like. Alternatively, cell fusion may be carried out in a commercial cell fusion device utilizing electric stimulation such as electroporation. After the fusion, the resultant cells are then diluted and cultured in HAT medium.

Hybridomas of interest are then selected from the fused cells. The fused cells surviving cultured in HAT medium would form colonies. The supernatant of each culture well is then collected and examine for the presence or absence of antibody titers to the polypeptide. As a method of confirmation, ELISA, EIA or RIA may be used. Once antibody-positive wells are identified, cells are then cultured in a HT medium, which does not contain aminopterin. After culturing for a while, antibody titers in the culture supernatant are confirmed again. Cells that are finally selected are then subject to cloning to obtain single cells. Clones that exhibit high specificity to the polypeptide are selected, and are proliferated to some extent to establish hybridomas.

The monoclonal antibodies produced by the hybridomas may be isolated or prepared by any known method. For example, antibodies may be prepared from cultured supernatant obtained by culturing hybridomas in a medium with low serum concentration. Alternatively, hybridomas may be injected into abdominal cavities of animals and the resultant abdominal dropsies are collected to prepare antibodies. Antibodies may be purified or isolated by methods that employ affinity column, gel filtration chromatography, ion exchange chromatography or the like. Any of these known methods may be appropriately selected or used in combination.

Alternatively, the present mAb may be produced by DNA cloning. DNA encoding the present mAb may be easily isolated and sequenced by use of conventional procedures, such as using oligonucleotide probes that are capable of binding specifically to genes encoding the heavy and light chains of the mAb. The hybridoma cells serve as a preferred source of such DNA. Once isolated, the DNA may be placed into expression vectors, which are then transfected into host cells such as *E. Coli* cells, simian COS cells or Chinese hamster ovary (CHO) cells or myeloma cells that do not produce immunoglobulin proteins, to synthesize the desired mAbs in the recombinant host cells.

The mAb thus produced and the DNA encoding such mAb can then be used to produce chimeric antibodies (e.g., bi-specific antibodies), humanized antibodies and/or antibody fragments derived thereof.

The major concern of a non-human origin mAb is its immunogenicity to the recipient, in some cases, caused dangerous allergic reactions. Most mAbs are of murine origin, and have been found to be immunogenic when injected to human. To reduce the immunogenicity of the non-human origin mAb, humanized antibodies are produced by attaching variable domains in the heavy and light chains of non-human origin mAbs onto the constant regions of human antibodies.

To create humanized mAbs, the DNA encoding such antibodies was isolated and sequenced, and then used to create humanized constructs.

According to preferred embodiments of the present disclosure, the VH and VL genes of the non-human origin mAb are constructed into human IgG1 vector. The resulting antibodies therefore have VH and VL regions derived from the non-human origin mAb, while the constant region genes (i.e., CK or CH1-H-CH2-CH3) are those of human IgG.

Once produced, the humanized mAbs may be purified according to standard procedures in the art, including crossflow filtration, affinity column chromatography, gel filtration and the like. It should be understood that the humanized mAbs shall perform in a manner identical or substantially similar to that of the non-human origin mAbs. Preferably, the humanized mAbs shall be more advantages to use in a human subject, as compared to the non-human version.

The first aspect of the present disclosure thus pertains to an mAb or a fragment thereof that is specific to Siglec-3 receptor (i.e., as an anti-Siglec-3 mAb or an anti-Siglec-3 antibody fragment). According to the embodiments of the present disclosure, the mAb comprises a VL region and a VH region, in which the VL region comprises CDR-L1, CDR-L2 and CDR-L3, and the VH region comprises CDR-H1, CDR-H2 and CDR-H3.

According to embodiments of the present disclosure, the present mAb is designated as antibody 10C8, in which the CDR-L1, CDR-L2 and CDR-L3 of the mAb respectively have the amino acid sequences of VYY, ISSAG (SEQ ID NO: 3) and QYFNFP (SEQ ID NO: 4), and the CDR-H1, CDR-H2 and CDR-H3 of the mAb respectively have the amino acid sequences of NNGW (SEQ ID NO: 5), GIGPYGGSTF (SEQ ID NO: 6) and SRFIGSYSHM (SEQ ID NO: 7).

Preferably, the VL region comprises the amino acid sequence at least 85% (i.e., 85%, 86%, 87%, 88%, 89%, 90%, 91%, 92%, 93%, 94%, 95%, 96%, 97%, 98%, 99% or 100%) identical to SEQ ID NO: 8, and the VH region comprises the amino acid sequence at least 85% (i.e., 85%, 86%, 87%, 88%, 89%, 90%, 91%, 92%, 93%, 94%, 95%, 96%, 97%, 98%, 99% or 100%) identical to SEQ ID NO: 9. As could be appreciated, the framework sequence of the VL and VH regions may vary (e.g., being substituted by conserved or non-conserved amino acid residues) without affecting the binding affinity and/or specificity of the present antibody. Preferably, the sequences of the framework is conservatively substituted by one or more suitable amino acid(s) with similar properties; for example, the substitution of leucine (an nonpolar amino acid residue) by isoleucine, alanine, valine, proline, phenylalanine, or tryptophan (another nonpolar amino acid residue); the substitution of aspartate (an acidic amino acid residue) by glutamate (another acidic amino acid residue); or the substitution of lysine (an basic amino acid residue) by arginine or histidine (another basic amino acid residue). According to the preferred embodiment, the VL and VH regions respectively comprises the amino acid sequences at least 90% identical to SEQ ID NOs: 8 and 9. More preferably, the VL and VH regions respectively comprises the amino acid sequences at least 95% identical to SEQ ID NOs: 8 and 9. In one working example of the present disclosure, the VL region has the amino acid sequence of SEQ ID NO: 8, and the VH region has the amino acid sequence of SEQ ID NO: 9.

The present mAb (i.e., anti-Siglec-3 mAb) is useful in the treatment or prophylaxis of HBV infection. Accordingly, also disclosed herein is a pharmaceutical composition or a medicament for preventing or treating HBV infection, and/or alleviate or ameliorate the symptoms associated with/caused by HBV infection. The pharmaceutical composition or medicament comprises an effective amount of the mAb or the fragment thereof in accordance with any aspect or embodiment of the present disclosure; and optionally, a pharmaceutically acceptable carrier.

Generally, the mAb/antibody fragment fragment of this invention is present at a level of about 0.1% to 99% by weight, based on the total weight of the pharmaceutical composition or medicament. In some embodiments, the mAb/antibody fragment of this invention is present at a level of at least 1% by weight, based on the total weight of the pharmaceutical composition or medicament. In certain embodiments, the mAb/antibody fragment is present at a level of at least 5% by weight, based on the total weight of the pharmaceutical composition or medicament. In still other embodiments, the mAb/antibody fragment is present at a level of at least 10% by weight, based on the total weight of the pharmaceutical composition or medicament. In still yet other embodiments, the mAb/antibody fragment is present at a level of at least 25% by weight, based on the total weight of the pharmaceutical composition or medicament.

The present pharmaceutical composition may be formulated into solid, semi-solid, or liquid forms, such as tablets, capsules, powders, granules, ointments, solutions, suppositories, and injections. As such, administration of the present mAb/antibody fragment can be achieved in various ways, including oral, buccal, rectal, parental, intravenous, intraperitoneal, and etc. administration. In pharmaceutical dosage forms, the present mAb/antibody fragment may be administered alone or in combination with other known pharmaceutically active agent to treat diseases and conditions caused by HBV infection. One of skilled person in the art is familiar with the various dosage forms that are suitable for use in each route. It is to be noted that the most suitable route in any given case would depend on the nature or severity of the disease or condition being treated.

The medicament or said pharmaceutical composition is prepared in accordance with acceptable pharmaceutical procedures, such as described in Remington's Pharmaceutical Sciences, 17$^{th}$ edition, ed. Alfonoso R. Gennaro, Mack Publishing Company, Easton, Pa (1985). Pharmaceutically acceptable carriers are those that are compatible with other ingredients in the formulation and biologically acceptable.

Applicable solid carriers may include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with an carrier having the necessary compression properties in suitable proportions and compacted in the shape and size desired. The powders and tablets preferably contain up to 99% of the active ingredient. Suitable solid carrier includes, for example, calcium phosphate, magnesium stearate, talc, sugars, lactose, dextrin, starch, gelatin, cellulose, methyl cellulose, sodium carboxymethyl cellulose, polyvinylpyrrolidine and the like.

The mAb/antibody fragment of the present invention may also be formulated into liquid pharmaceutical compositions or medicaments, which are sterile solutions or suspensions that can be administered by, for example, intravenous, intraarterial, intramuscular, subcutaneous, intrathecal, intraperitoneal, or intra-cerebella injection.

The pharmaceutical compositions or medicaments of this disclosure are formulations suitable for parenteral administration, such as administration by injection, which includes, but is not limited to, subcutaneous, bolus injection, intramuscular, intraperitoneal and intravenous injection. The pharmaceutical compositions or medicaments may be formulated as isotonic suspensions, solutions or emulsions in oily or aqueous vehicles, and may contain formulary agents such as suspending, stabilizing or dispersing agents. Alternatively, the compositions or medicaments may be provided in dry form such as powders, crystallines or freeze-dried solids with sterile pyrogen-free water or isotonic saline before use. They may be presented in sterile ampoules or vials.

When the present mAb/antibody fragment is formulated to be administered by intravenous, cutaneous or subcutaneous injection, the mAb will be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition or medicament for intravenous, cutaneous, or subcutaneous injection should contain, in addition to the present mAb/antibody fragment, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition or medicament of the invention may also contain stabilizers, preservatives, buffers, antioxidants, or other additives known to those of skill in the art. The duration of intravenous therapy using the pharmaceutical composition or medicament of the invention will vary, depending on the severity of the disease being treated and the condition and potential idiosyncratic response of each individual subject. It is contemplated that the duration of each application of the present mAb will be in the range of 12 to 24 hours of continuous intravenous administration. Ultimately the attending physician will decide on the appropriate duration of intravenous therapy.

Another aspect of the present disclosure pertains to a method of preventing and/or treating HBV infection in a subject. The method comprises administering to the subject an effective amount of the mAb/antibody fragment, pharmaceutical composition or medicament of the present disclosure.

The effective dose administered to the subject is from about 0.01 to 1,000 mg/Kg body weight of the subject, such as 0.01, 0.02, 0.03, 0.04, 0.05, 0.06, 0.07, 0.08, 0.09, 0.1, 0.2, 0.3 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, or 1,000 mg/Kg body weight of the subject; preferably, about 0.1 to 100 mg/Kg body weight of the subject. The dose can be administered in a single aliquot, or alternatively in more than one aliquot. The skilled artisan or clinical practitioner may adjust the dosage or regime in accordance with the physical condition of the patient or the severity of the diseases.

According to some embodiments of the present disclosure, HBV infection suppresses the immune response of the subject, and the treatment of the present mAb (i.e., anti-Siglec-3 mAb) reverses the HBV-induced immunosuppression. In these embodiment, the present anti-Siglec-3 mAb is useful in blocking the interaction between HBV and Siglect-3 thereby activating/improving the host immunity to eradicate HBV particles in the subject. Accordingly, the present anti-Siglec-3 mAb provides an potential means to prevent or treat the HBV infection, and/or alleviate or ameliorate the symptoms associated with/caused by HBV infection.

Basically, the subject treatable by the present method is a mammal, for example, human, mouse, rat, guinea pig, hamster, monkey, swine, dog, cat, horse, sheep, goat, cow, and rabbit. Preferably, the subject is a human.

The present mAb (i.e., anti-Siglec-3 mAb) may be administered to the subject by a route selected from the group consisting of oral, enteral, nasal, topical, transmucosal, and parenteral administration, in which the parental administration is any of intramuscular, intravenous, or intraperitoneal injection.

As would be appreciated, the present method can be applied to the subject, alone or in combination with additional therapies that have some beneficial effects on the prevention or treatment of HBV infection. Depending on the intended/therapeutic purpose, the present method can be applied to the subject before, during, or after the administration of the additional therapies.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

Blood Donors

Naïve un-treated CHB patients (n=6) with HBeAg-positive (HBV DNA $>2\times10^7$ IU/mL) admitted to China Medical University Hospital were enrolled for this study. All of the patients were negative for other viral infections, including hepatitis C virus (HCV), human immunodeficiency virus (HIV), cytomegalovirus (CMV), and Epstein-Barr virus (EBV). Healthy donors (n=6) were enrolled from Taiwan blood center. This study was approved by the local ethics committee, and the written informed consent was obtained from all of the participants.

Plasmids and Fusion Proteins

The DNA fragments of human Siglec-3/-7 extracellular domain (ECD) were amplified by reverse transcription-PCR from human GM-Mφ and subcloned into the pSecTag2-hIgG vector to generate the recombinant Siglec-3/-7 ECD.Fc fusion proteins. The recombinant Siglec-3/-7/-9 ECD.Fc fusion proteins were overexpressed by the FreeStyle 293 Expression System (Invitrogen) according to vendor's instruction. The culture supernatants were harvested at day 3 and 5 post transfection, and the recombinant fusion proteins were purified by Protein A column.

Purification and Quantification of HBV Virus

HBV was purified from blood samples of chronic hepatitis B (CHB) patients and HBV-transgenic mice, respectively. The protocol for HBV was purified by conventional method. HBV viral load was determinate by RT-PCR according to a standard HBV plasmid. HBsAg level was quantified by the HBsAg ELISA kit.

Identify Glycan Structure on HBsAg by Nano-LC-MS/MS

Purified HBV from CHB patients and transgenic mice was loaded on 12% SDS-PAGE, and the gel was cut into species according to the weight of HBsAg followed by trypsin and chymotrypsin digestion. High resolution and high mass accuracy nano-flow LC-MS/MS experiments were done on a LTQFT Ultra (Linear quadrupole ion trap Fourier transform ion cyclotron resonance) mass spectrometer equipped with a nano-electrospray ion source, an Agilent 1100 Series binary high-performance liquid chromatography pump, and a Famos autosampler. The digestion solution was injected (6 µl) at 10 µl/min flow rate on to a self-packed precolumn (150 µm I.D.×20 mm, 5 µm, 100 Å). Chromatographic separation was performed on a self-packed reversed phase C18 nano-column (75 µm I.D.×300 mm, 5 µm, 100 Å) using 0.1% formic acid in water as mobile phase A and 0.1% formic acid in 80% acetonitrile as mobile phase B operated at 300 nl/min flow rate. Survey full-scan MS condition: mass range m/z 320-2000, resolution 50,000 at m/z 400. The five most intense ions were sequentially isolated for MS2 by LTQ. Electrospray voltage was maintained at 1.8 kV and capillary temperature was set at 200° C.

Removal of Sialic Acid from HBV and Sialoglycan by Sialidase

Sialidase S and sialidase C were used to remove sialoglycan from HBV or sialoglycans, respectively. Sialidase S releases only α(2-3)-linked Neu5Ac, while Sialidase C release both α(2-3) and α(2-6)-linked Neu5Ac. The sialidase-treated substrates were used for HBV-Siglec-3 binding assay and competition assay.

Interaction Between HBV and Siglec.Fc Fusion Proteins

HBV (10' copies/mL) was incubated with recombinant Siglec-3/-7/-9 ECD.Fc fusion proteins, respectively, for 16 hours at 4° C., followed by incubation with Sepharose-conjugated Protein A beads for immunoprecipitation. The samples were fractionated on 12% SDS-PAGE before blotting to PVDF membrane and incubated in blocking buffer (0.05% Tween 20 in TBS containing 5% BSA) at 4° C. overnight. Blots were incubated with HRP-conjugated polyclonal goat-anti-HBs Ab for 1 hour at room temperature, followed by incubation with Streptavidin-HRP (1:10000 dilution) for another 1 hour at room temperature, and were visualized by ECL.

Competition Assay

Siglec ECD.Fc fusion proteins (5 µg) were coated on microtitre plates, followed by addition of HBsAg (100 ng) in the presence various concentrations of following glycans: Neu5Ac(α2-6)-Gal-GlcNAc, Neu5Ac(α2-3)-Gal-GlcNAc, and Gal-GlcNAc at 4° C. for 12 hours with Protein free blocking buffer. The sialidase-treated and un-treated sialyglycans were used for competition assay.

Determination of Receptor-Virus Interaction by Bio-Layer Interferometry (BLI)

The interaction between human Siglec.Fc fusion protein and HBV was determined by the Bio-layer interferometry. In brief, the biosensor was immobilized with the Siglec.Fc fusion protein, and the binding between the Siglec.Fc and HBV was performed with running buffer (10 mM Tris HCl, 150 mM NaCl, 2 mM $CaCl_2$, 2 mM $MgCl_2$, pH 7.4) at room temperature. The valence between HBV and human Siglec-3 was determined, which correlates the strength of multivalent association with that of monovalent association as shown in the following:

KA, surf=F $(S \times 10^{-2})^{n-1} \times$(KA, mono)$^n$, where KA, surf is thereciprocal of KD (HBV and Siglec-3), KA, mono is the reciprocal of KD (Biantennary a2-6 linked sialylglycopeptide and Siglec-3); n is the number of valency number; F is the statistic factor in the system and S is equal to 40(Å), which is estimated according to crystal structure of Siglec-3 published on RCSB protein data bank (Number: 5J0B). Three individual BLI results were used to calculate out the n (number of valency).

Generation and Characterization of Anti-Siglec mAbs and Selection of Antagonistic Antibody Anti-Siglec mAbs were produced from phage-displayed synthetic antibody libraries. The generic human antibody was constructed based on combining the functional scFv variants with human IgG and produced by the FreeStyle 293 Expression System.

APC-conjugated anti-Siglec-3 and human IgG (prepared by APC-conjugated kit), were used to for flow cytometry to determine their binding to monocyte-derived dendritic cells (moDCs). Identification of agonist and antagonist clones of anti-Siglec-3 mAbs was based on their inhibitory effects on TLR2-stimulated cytokine secretion from moDCs. In brief, moDCs were seeded in culture plate for 24 hours, followed by incubation with anti-Siglec mAb for 1 hour before addition of pam3csk4 (0.05 µg/mL) and incubated for further 24 hours. Cytokine level in the supernatants was determined by ELISA kits.

Cell Culture

Peripheral blood mononuclear cells (PBMCs) were isolated from the whole blood of healthy human donors and CHB patients by standard density-gradient centrifugation. To prepare primary macrophages, $CD14^+$ cells were purified from PBMCs by high-gradient magnetic sorting with anti-CD14 microbeads. Cells were then incubated in complete RPMI 1640 medium with 10% FCS supplemented with human GM-CSF/IL-4 for 6-7 days to generate moDCs.

To test the inhibitory effect of HBV, moDCs ($6 \times 10^4$ per well) were incubated with HBV for 24 hours before addition of Pam3csk4 (0.05 µg/mL) or poly (I.C) (100 µg/mL)+IFN-γ (100 ng/mL) for another 24 hours. To identify the agonistic and antagonistic anti-Siglec-3 mAbs, moDCs ($6 \times 10^4$ per well) and PBMC ($6 \times 10^4$ per well) of CHB patient were incubated with anti-Siglec mAb for 1 hour, followed by adding HBV for 24 hours before addition of Pam3csk4 (0.05 µg/mL) or poly (I.C) (100 µg/mL) for another 24 hours. Supernatants were collected to determine cytokine level by ELISA kits.

Confocal Microscopy

MoDC ($2 \times 10^5$ cells) and PBMCs of CHB patients were incubated with HBV (109 copies/mL) isolated from CHB patient for 1 hour with or without anti-Siglec-3 mAb (3 µg/mL, clone 10C8) on ice. Cells were washed and fixed at 4° C. for 1 hour, followed by incubating in permeability buffer (0.5% Triton X-100 in PBS) for 15 hours and blocking buffer (3% BSA) at room temperature for 1 hour subsequently before addition of primary antibodies. After incubation at 4° C. for 24 hours, cells were incubated with secondary antibody at room temperature for another 1 hour, followed by addition of phalloidin (1 unit/µL) and Hoechst 33342 for 10 minutes before observation under an Leica SP5 confocal microscope.

Fluorescence Resonance Energy Transfer (FRET) and Fluorescence Lifetime Imaging (FLIM)

Siglec-3 (specified as donor) was incubated with primary antibody at 4° C. for 24 hours, followed by incubation with donkey anti-mouse (H+L) Alexa-Fluor 647-conjugated secondary antibody at room temperature for 1 hour. HBsAg (specified as acceptor) was incubated with primary antibody 100 µL of 10 µg/mL at 4° C. for 24 hours followed by addition of donkey anti-Goat (H+L) Alexa-Fluor 546-conjugated secondary antibody antibody at room temperature for 1 hour. After staining, cells were washed with PBS and resuspended in mounting solution and covered by coverslips.

For FLIM-FRET analysis, FLIM was recorded on a Leica SP5 confocal microscope. Fluorescence lifetimes were measured in cells expressing only the FRET donor, and cells expressing the combination of FRET donor and acceptor. Samples were pulsed with a laser (488 nm) and emitted wave length (500 to 550 nm) was collected. 10,000 photons were recorded for each sample. FRET efficiency (E) was calculated according to the equation: $E=1-(\tau DA/\tau D)$, where $\tau DA$ is the mean fluorescence lifetime of cells co-expressing FRET donor and acceptor, and $\tau D$ is the mean fluorescence lifetime of cells expressing FRET donor only.

Detection of Siglec-3-Associated SHP-1 and SHP-2 in HBV-Treated moDCs

MoDCs were incubated with HBV, followed by resuspension in lysis buffer before incubation with anti-Siglec-3 polyclonal antibody, followed by immunoprecipitation using Protein A-conjugated Sepharose. The immunoprecipitates were fractionated on SDS-PAGE, followed by transfer to PVDF membrane before probed with anti-SHP-1 and SHP-2 antibody, respectively. Immunoblots were developed by incubating with HRP-conjugated anti-rabbit IgG antiserum and enhanced chemiluminescence detection reagents subsequently. To detect the total amount of Siglec-3, blot was stripped with Re-Blot Plus Strong solution before probed with mouse anti-Siglec-3 antibody.

Statistical Analysis

Values are expressed as mean±standard deviation. All experiments repeated at least 3 times. The results were evaluated by Student t test. P value of 0.05 was regarded as significant.

Example 1 Glycan Structure on HBsAg

To understand the potential difference of sialyglycan in hHBV and mHBV, viral particles were purified from serum samples of CHB patients (hHBV) and transgenic mice (mHBV), respectively, by CsCl2 ultracentrifugation, followed by nano-flow LC-MS/MS and GlycoSeq software to determine glycan structures.

Two peptides with overlapping sequences derived from hHBV surface antigen (hHBsAg) were found to containing N-glycan. The first peptide had the amino acid sequence of SEQ ID NO: 1 ($T_{140}KPTDGN_{146}CTCIPIPSSW_{156}$, the N-glycan was located on Asn-146; and the second peptide had the amino acid sequence of SEQ ID NO: 2 ($P_{142}SDGN_{146}CTCIPIPSSWAFGK_{160}$, the N-glycan was located on Asn-146). The T/S$_{143}$ mutation suggested the presence of HBV mutants in CHB patients' sera. For the first peptide, the signal at mass to charge ratio (m/z) 1068.94 represented the presence of GlcNAc, m/z 656.92 represented the presence of Neu5Ac-Gal-GlcNAc, and m/z 1515.02-1923.80 represented the fragmentation of the extended branch with sialylated glycan (data not shown). This information suggested the presence of biantennary N glycans: Neu5Ac-Gal-GlcNAc-Man link to GlcNAc in hHBsAg. The linkage of terminal sialic acid to galactose was further determined by Pseudo-MS Mass Spectrometry. The low m/z 274.12 and m/z 292.15 suggested the presence of Neu5Ac ($\alpha$2-6)-Gal-GlcNAc (data not shown). In addition, approximately 45% peptides contained biantennary N-glycans conjugated with two sialic acids (biS2, 27.6%) or one sialic acid (biS1, 17.9%) (FIG. 1, Panel A). Similar observation was found in the second peptide (FIG. 1, Panel B). In contrast, the first peptide derived from mHBV surface antigen (mHBAg) did not contain N-glycan, even though the peptide sequence for glycan conjugation was identical (FIG. 1, Panel C).

The data indicated that HBsAg from CHB patient (denoted as hHBsAg) contained the biantennary Neu5Ac($\alpha$2-6)GalGlcNAcMan conjugated to Asn-146 on small S antigen of hHBV, while mHBsAg from HBV transgenic mice was absent of biantennary Neu5Ac($\alpha$2-6)GalGlcNAcMan at the same position.

Example 2 Interaction Between HBV Asn-146 Sialyglycan and Members of Human Siglecs Since hHBV biantennary glycan is similar to the ligands of human Siglec-3,-7,-9, whether hHBV interacts with these myeloid Siglecs, which are highly expressed in dendritic cells and other myeloid cells, was investigated in this example.

Figure 2:
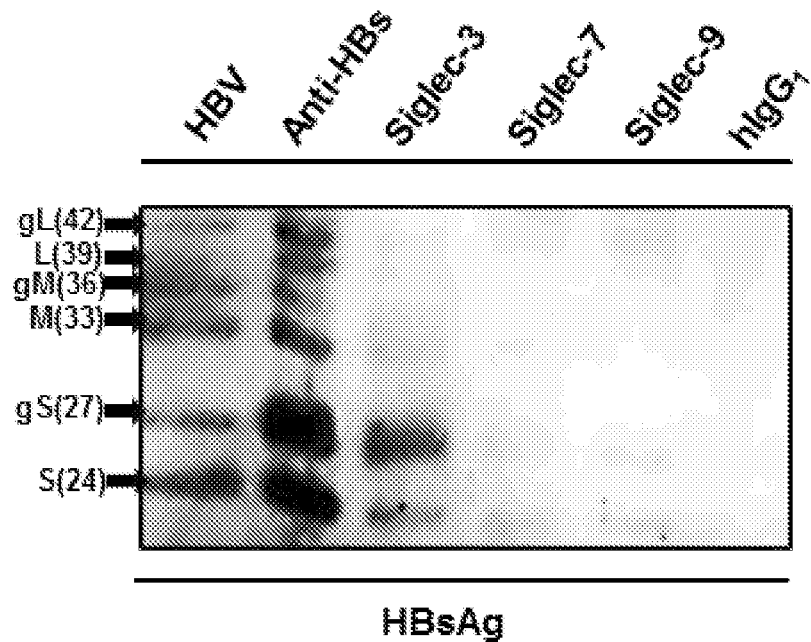
Figure 2:
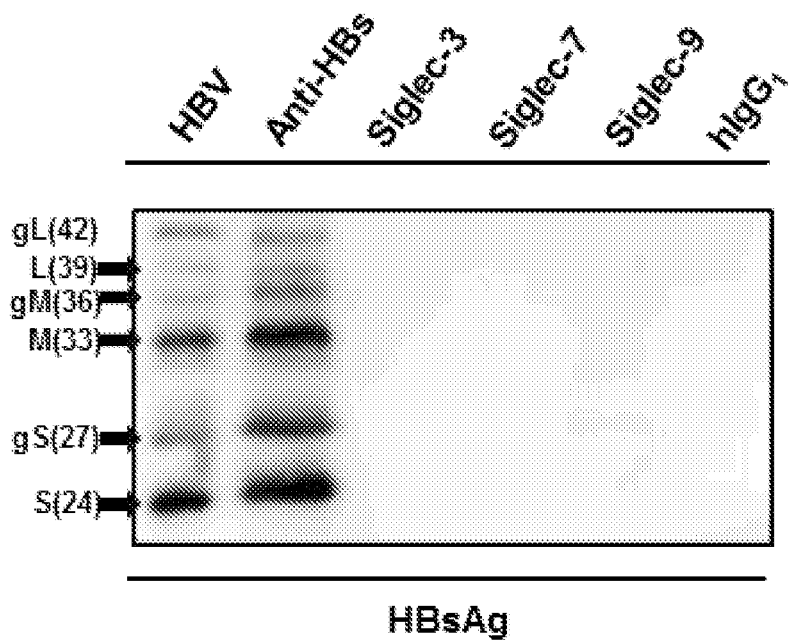
Figure 2:
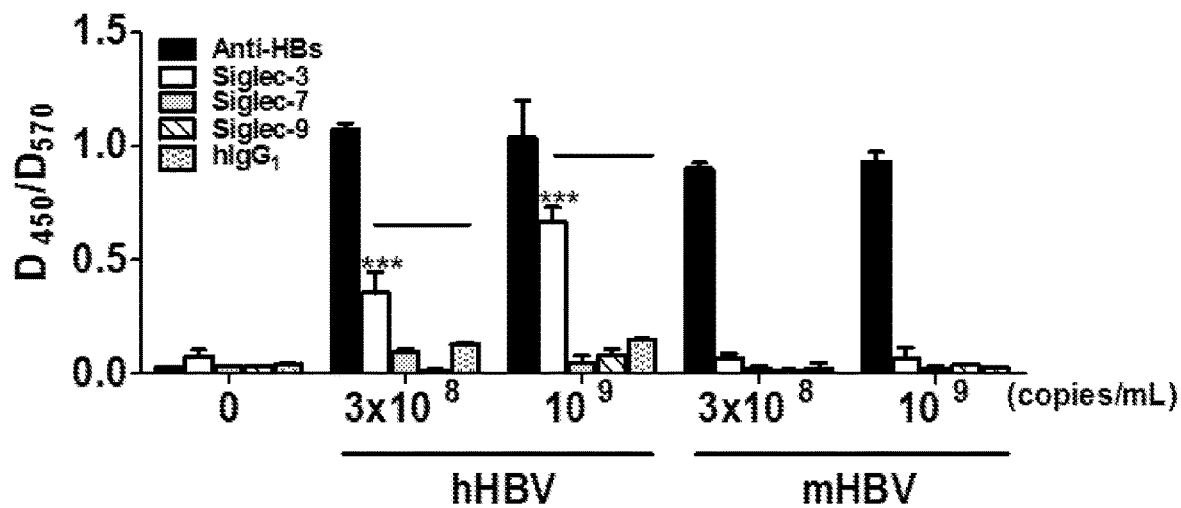
Figure 2:
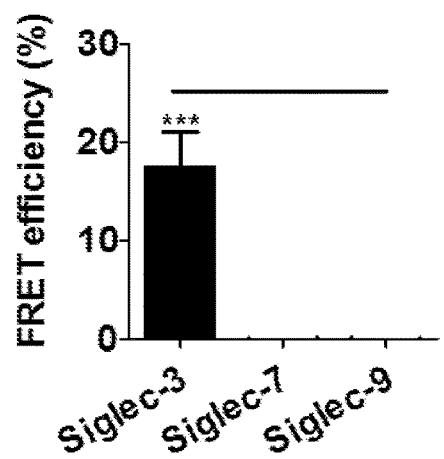
Figure 2:
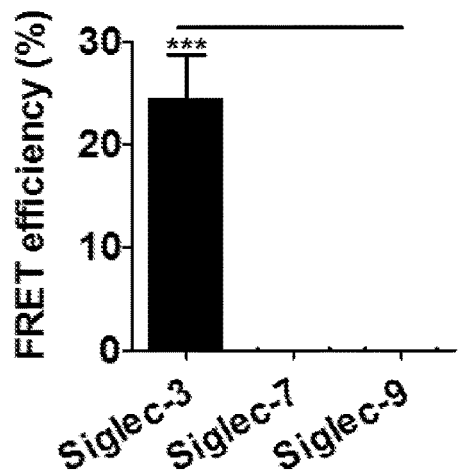
Figure 2:
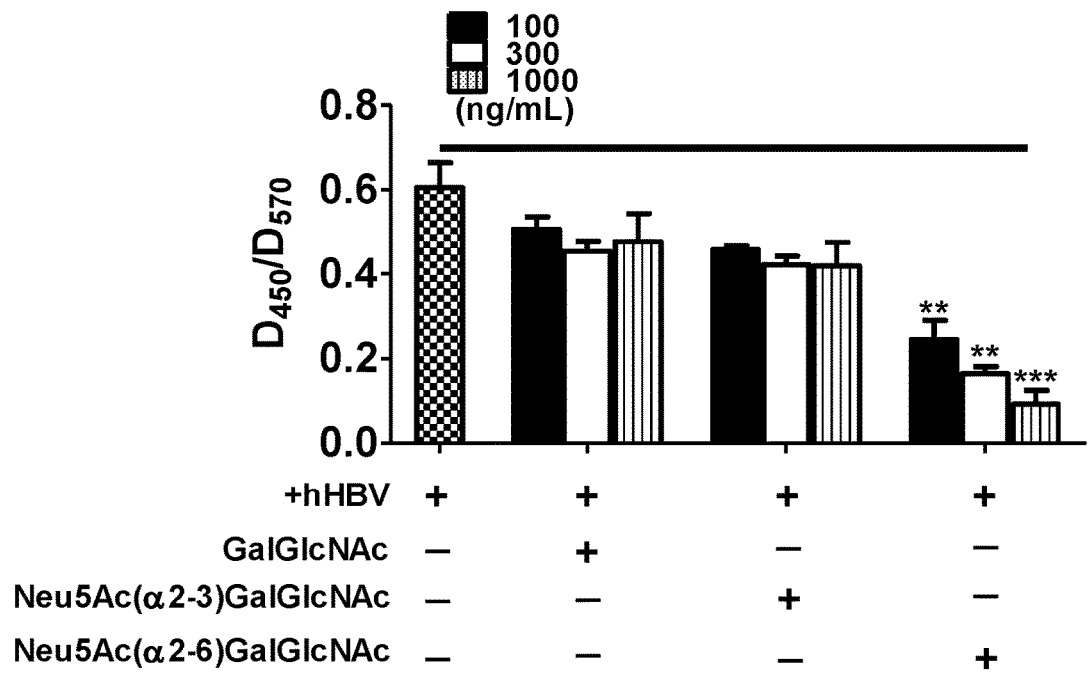
Figure 2:
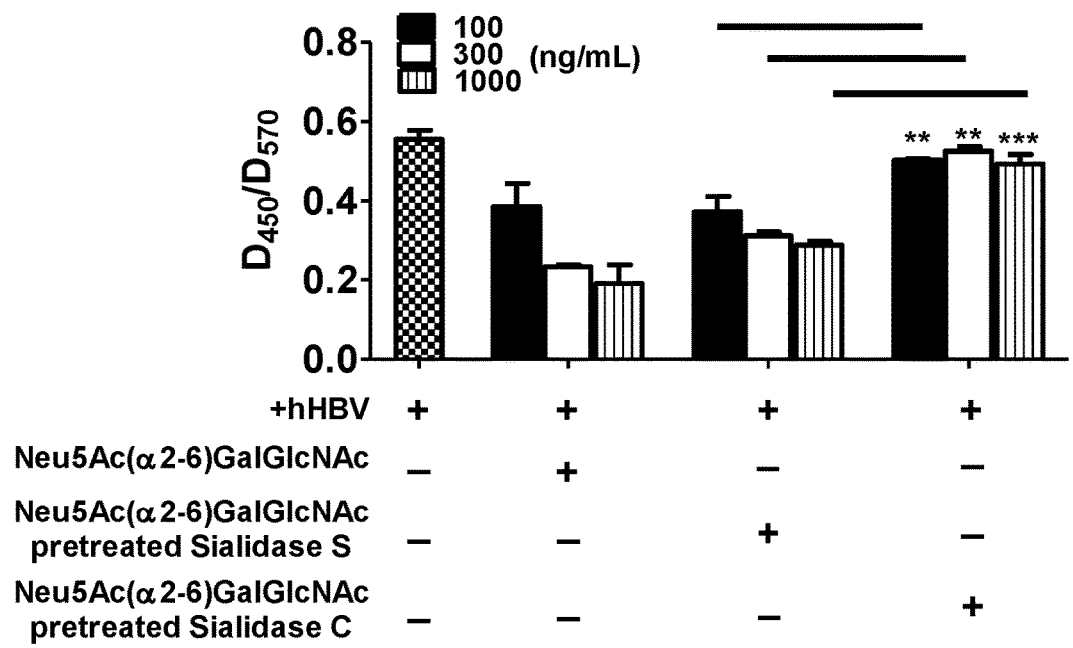
Figure 2:
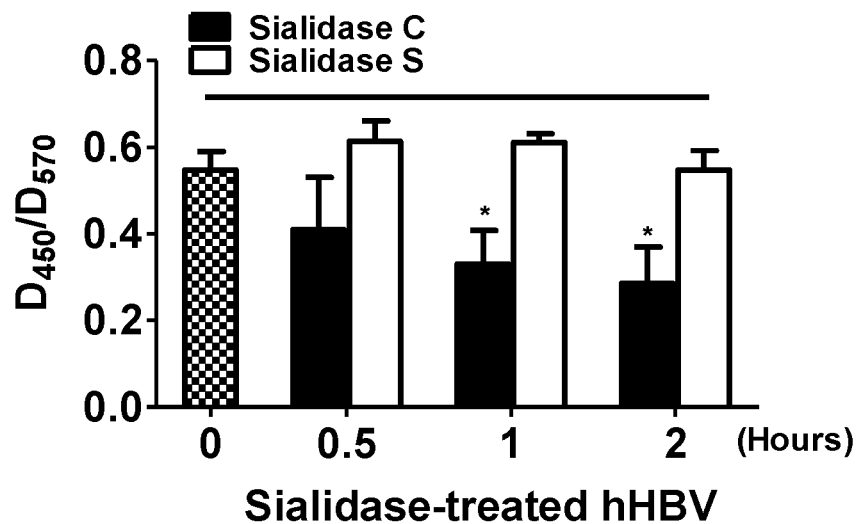

Recombinant Siglec ECD.Fc fusion proteins were incubated with hHBV to examine their ability to pull down hHBV from supernatant. Anti-HBsAg polyclonal Ab was able to pull down all the glycosylated and non-glycosylated HBsAg (small, middle, and large), and human Siglec-3.Fc mainly pulled down glycosylated small HBsAg(h) (gs, 27 KDa) (FIG. 2, Panel A); these data suggested that Siglec-3 preferentially bound to hHBV sialoglycan in small HBsAg. However, Siglec-7.Fc and Siglec-9.Fc cannot pull down under the same condition (FIG. 2, Panel A), and these observations suggested that hHBV preferentially bound to Siglec-3 via sialoglycan on small HBsAg (FIG. 2, Panel A).

It is interesting to find that both glycosylated and non-glycosylated HBsAg were detected in mHBV (FIG. 2, Panel B), even though sialoglycans at Asn-146 of mHBV was absent. This observation was in accord with previous report that additional glycosylation sites were detected in amino acid residues Asn-129, Asn-130 and Asn-131. The binding specificity of myeloid Siglecs with mHBV was further determined by immunoprecipitation and ELISA. However, none of the Siglecs could pull down mHBV (FIG. 2, Panel B), neither bound to all the three Siglecs by ELISA (FIG. 2, Panel C).

To confirm the specific interaction between hHBV and human Siglec-3 ex vivo, peripheral blood cells were isolated from CHB patients, and double stained by anti-HBsAg with secondary antibody conjugated with Alexa-Fluor 546 and anti-Siglec-3 mAb with secondary antibody conjugated with Alexa-Fluor 488. The cells were contoured by phalloidin. The data indicated that HBsAg was only detected in Siglec-3$^+$ cells, and was colocalized with HBsAg (data not shown). This observation suggested that hHBV bound to Siglec-3$^+$ human myeloid cells. The direct association between hHBV and Siglec-3 was further revealed by fluorescence resonance energy transfer (FRET). The data indicated that high energy transfer was only detected between hHBV with Siglec-3, but not Siglec-7 and Siglec-9 (FIG. 2, Panels D and E). Furthermore, addition of Siglec-3 ligand (Neu5Ac(α2-6)Gal-GlcNAc) inhibited Siglec-3-HBV interaction in a dose-dependent manner, while Neu5Ac(α2-3)GalGlcNAc and GalGlcNAc did not inhibit Siglec-3-HBV interaction under the same condition (FIG. 2, Panel F). To further confirm that hHBV-Siglec-3 interaction is via α2-3-linked sialic acid, Sialidase S (release α2-3 sialic acid) and Sialidase C (release both α2-3 and α2-6 sialic acid) were added to remove sialic acid from Neu5Ac(α2-6)GalGlcNAc glycan and hHBV, respectively. The data demonstrated that Sialidase C-, but not sialidase S-treated, Neu5Ac(α2-6)GalGlcNAc glycan lost its inhibitory effect in Siglec-3-HBV interaction (FIG. 2, Panel G), and Sialidase C reduced hHBV binding to Siglec-3 (FIG. 2, Panel H).

Collectively, these results demonstrated that the interaction between hHBV and Siglec-3 was mainly via terminal α2-6 sialic acid on HBsAg-associated sialoglycan.

Example 3 Determination of Binding Affinity Between HBV and Human Siglecs

The binding affinity between human Siglec-3 and hHBV virion was determined in this example. The equilibrium dissociation constant (KD) between recombinant Siglec-3.Fc (Siglec-3 was dimeric) and monomeric Neu5Ac(α2-6)GalGlcNAc was 1.59 (±0.97)×10⁻³, while the KD between Siglec-3.Fc and biantennary Neu5Ac(α2-6)GalGlcNAc was 9.59 (±1.45)×10⁻⁵ (Table 1).

TABLE 1

Kinetic interaction of Siglec-3.Fc and Neu5Ac(α2-6)GalGlcNAc glycans

| Immobilized Fc-Lectin (nm) | Neu5Ac (α2-6) GalGlcNAc | Ka (1/Ms) | Kd (1/s) | KD (M)* |
|---|---|---|---|---|
| Siglec-3 | Monomeric | 5.44 (±2.14) × 10⁰ | 6.02 (±0.45) × 10⁻³ | 1.59 (±0.97) × 10⁻³ |
|  | Bianntenary SGP | 2.31 (±0.10) × 10⁴ | 2.21 (±0.86) × 10⁰ | 9.59 (±1.45) × 10⁻⁵ |

Ka: Rate constants for association.
Kd : Rate constants for dissociation.
KD: Equilibrium dissociation constant. Results are expressed as means ± s.d. from three independent experiments.

The KD between recombinant Siglec-3 and human HBV (hHBV) virions increased to 1.15 (±0.11)×10⁻¹⁰ (Table 2). In contrast, mouse HBV (mHBV) virions did not bind to human Siglec-3 under the same condition (Table 3).

TABLE 2

Kinetic interaction of recombinant Siglec-3 and hHBV

| Immobilized Fc-Lectin (nm) | Ka (1/Ms) | Kd (1/s) | KD (M)* |
|---|---|---|---|
| Anti-HBS | 8.03 (±0.10) × 10⁶ | 4.17 (±0.29) × 10⁻⁵ | 5.19 (±0.37) × 10⁻¹² |
| Siglec-3 | 3.11 (±0.10) × 10⁶ | 3.58 (±0.31) × 10⁻⁴ | 1.15 (±0.11) × 10⁻¹⁰ |
| Siglec-7 | N/A | N/A | N/A |

TABLE 2-continued

Kinetic interaction of recombinant Siglec-3 and hHBV

| Immobilized Fc-Lectin (nm) | Ka (1/Ms) | Kd (1/s) | KD (M)* |
|---|---|---|---|
| Siglec-9 | N/A | N/A | N/A |
| hIgG₁ | N/A | N/A | N/A |

Ka: Rate constants for association.
Kd : Rate constants for dissociation.
KD: Equilibrium dissociation constant. Results are expressed as means ± s.d. from three independent experiments.

TABLE 3

Kinetic interaction of recombinant Siglec-3 and mHBV

| Immobilized Fc-Lectin (nm) | Ka (1/Ms) | Kd (1/s) | KD (M) |
|---|---|---|---|
| Anti-HBS | 8.12 (±0.01) × 10⁶ | 2.55 (±0.29) × 10⁻⁵ | 3.14 (±0.36) × 10⁻¹² |
| Siglec-3 | N/A | N/A | N/A |
| Siglec-7 | N/A | N/A | N/A |
| Siglec-9 | N/A | N/A | N/A |
| hIgG₁ | N/A | N/A | N/A |

Ka: Rate constants for association.
Kd : Rate constants for dissociation.
KD: Equilibrium dissociation constant. Results are expressed as means ± s.d. from three independent experiments.

The valence (N) between HBV and the recombinant Sigelc-3.Fc was '2', suggesting that each monomeric Siglec-3 bound to one biantennary Neu5Ac(α2-6)GalGlcNAc. In contrast, hHBV did not bind to other Siglec-7 and Siglec-9 under the same condition. Removing α2-6 linked Neu5Ac from hHBV by sialidase C abolished the binding between Siglec-3 with hHBV (Table 4).

TABLE 4

Kinetic interaction of Siglec-3 and specified hHBV

| Immobilized Fc-Lectin (nm) | hHBV | Ka (1/Ms) | Kd (1/s) | KD (M) |
|---|---|---|---|---|
| Siglec-3 | Untreat | 1.18 (±0.12) × 10⁶ | 6.97 (±0.46) × 10⁻⁴ | 5.91 (±0.74) × 10⁻¹⁰ |
|  | Sialidase S treated | 7.11 (±0.81) × 10⁵ | 2.73 (±0.31) × 10⁻⁴ | 3.84 (±0.61) × 10⁻¹⁰ |
|  | Sialidase C treated | N/A | N/A | N/A |

Ka: Rate constants for association.
Kd : Rate constants for dissociation.
KD: Equilibrium dissociation constant. Results are expressed as means ± s.d. from three independent experiments.

The data indicated that hHBV virion bound to Siglec-3 via terminal α2-6 sialic acid of the biantennary Neu5Ac(α2-6)GalGlcNAc.

Example 4 Suppression of Cytokine Secretion in TLR Ligand Stimulated-moDC by hHBV The role of Asn-146 sialoglycan in cytokine secretion of human monocyte-derived dendritic cells (moDCs) stimulated with TLR ligands, which are potent activator of immune cells, was investigated in this example.

Figure 3:
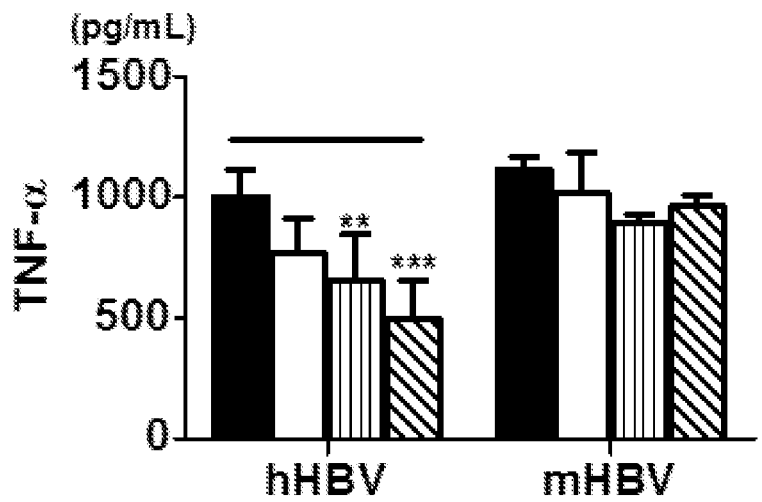
Figure 3:
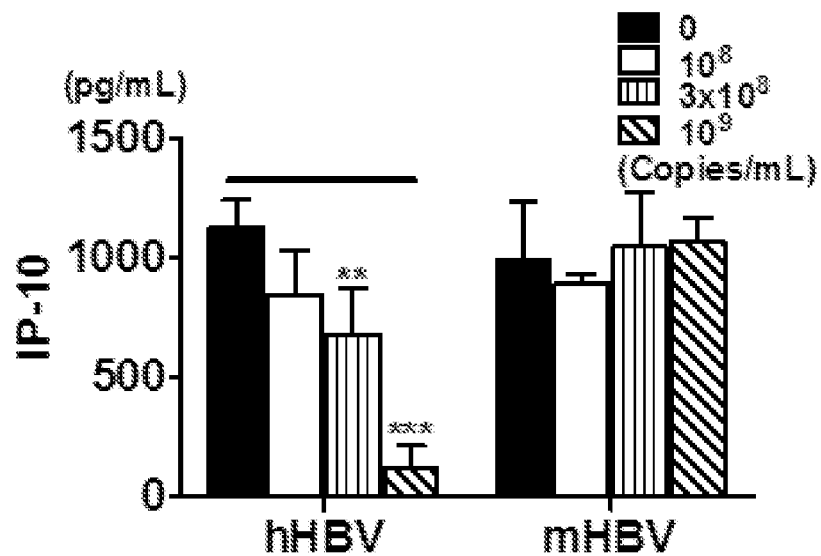
Figure 3:
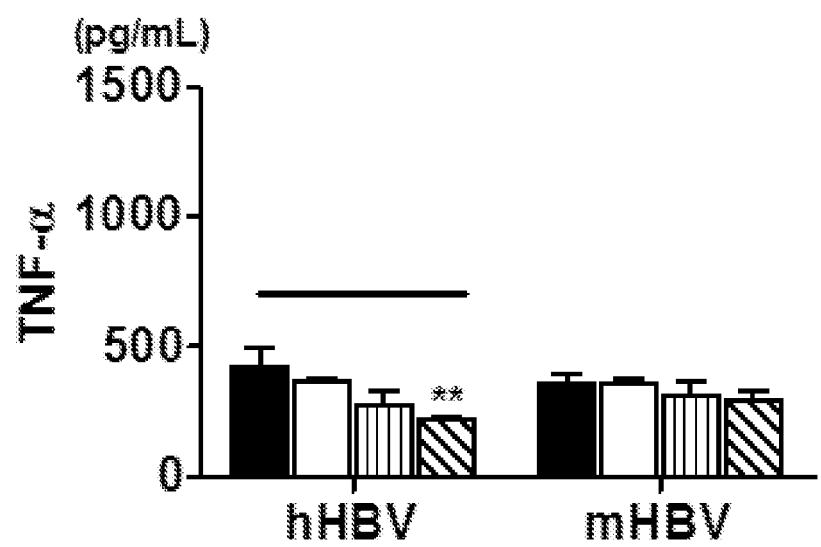
Figure 3:
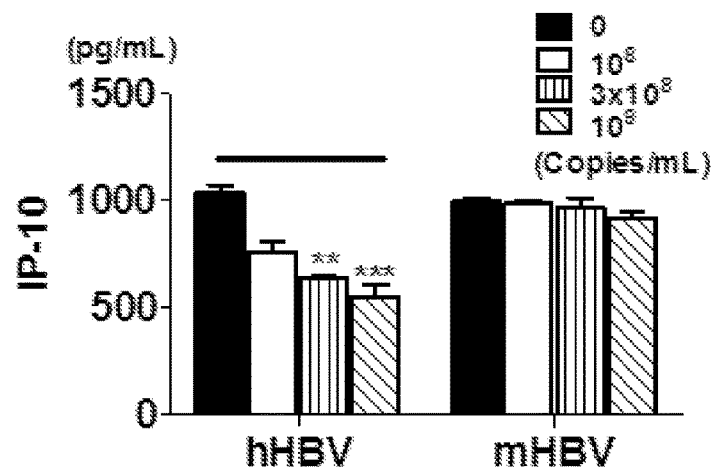
Figure 3:
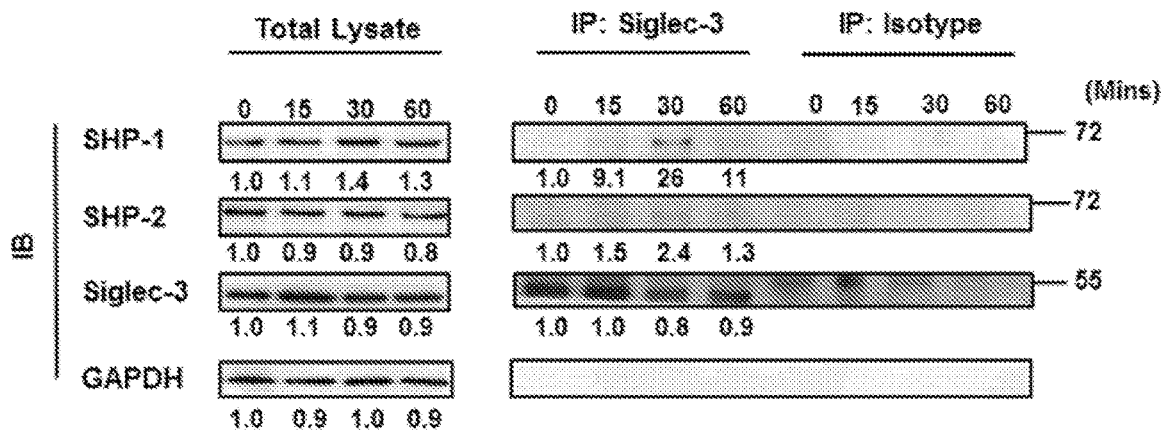
Figure 3:
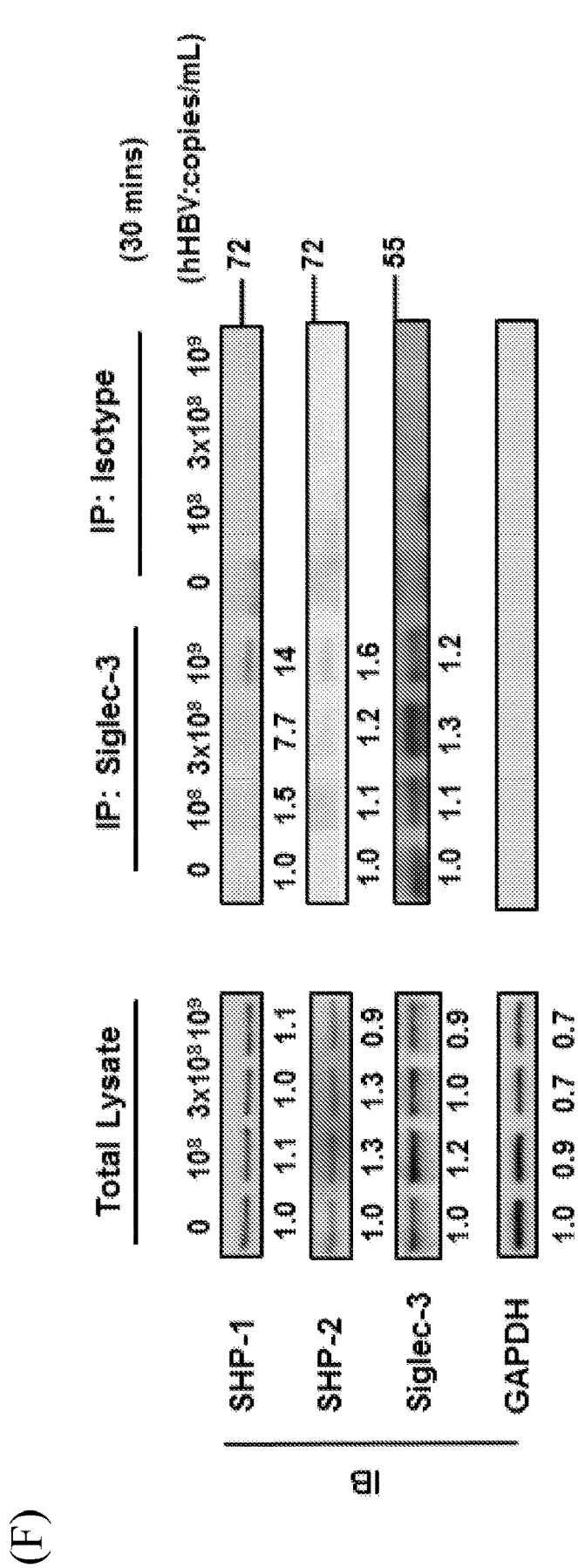

MoDCs respectively isolated from CHB patients and transgenic mice were incubated with Pam3csk4 (TLR-2 ligand) and poly (I.C) (TLR-3 ligand) in conjunction with interferon-α (IFN-α). While the production of tumor necrosis factor (TNF-α) and interferon gamma-induced protein 10 (IP-10) was suppressed by hHBV in a dose-dependent manner, mHBV did not have suppressive effect under the same condition (FIG. 3, Panels A to D). This observation suggested that hHBV-mediated suppression may be via activation of Siglec-3. To confirm this speculation, moDC were incubated with hHBV for various time points, followed by coimmunoprecipitation using anti-Siglec-3 mAb to detect SUP-1 and SHP-2, which were recruited by ITIM-motif after activation of Siglec-3 (FIG. 3, Panel E). The data showed that the signals of SHP-1 and SHP-2 were detected at 15 minutes, reached peak at 30 minutes, and then decreased at 60 minutes post-incubation with hHBV (FIG. 3, Panel E). In addition, hHBV recruited SUP-1 and SUP-2 in a dose-dependent manner (FIG. 3, Panel F).

These observations suggested that hHBV-mediated suppression on TLR ligands-induced cytokine secretion was via Siglec-3-induced suppressive signals.

Example 5 Evaluating the Effect of Anti-Siglec-3 mAb on HBV Infection 5.1 Production and Characterization of Anti-Human Siglec-3 mAbs In this example, four monoclonal antibodies against Siglec-3 were produced so as to identify antagonistic anti-Siglec-3 mAb thereby blocking HBV-mediated immunosuppression.

To reach this purpose, anti-human Siglec-3 mAbs were selected from phage-displayed synthetic human antibody libraries, and evaluated the inhibitory effect thereof on HBV-mediated immunosuppression. Among the positive clones selected, clone 2B9 and clone 10C8 displayed highest mean fluorescence intensity (MFI) to moDCs by flow cytometry (data not shown). According to the sequencing data, the VL and VH regions of the mAb 10C8 respectively comprised the amino acid sequences of SEQ ID NOs: 8 and 9, in which the CDR-L1 to CDR-L3 respectively comprised the amino acid sequence of VYY, ISSAG (SEQ ID NO: 3) and QYFNFP (SEQ ID NO: 4); and the CDR-H1 to CDR-H3 respectively comprised the amino acid sequence of NNGW (SEQ ID NO: 5), GIGPYGGSTF (SEQ ID NO: 6), and SRFIGSYSHM (SEQ ID NO: 7).

Figure 4:
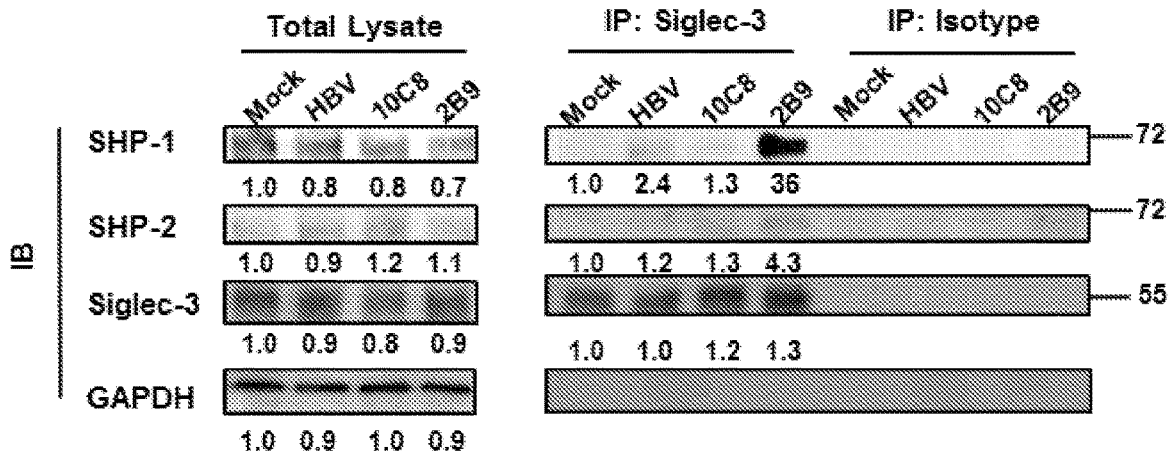
Figure 4:
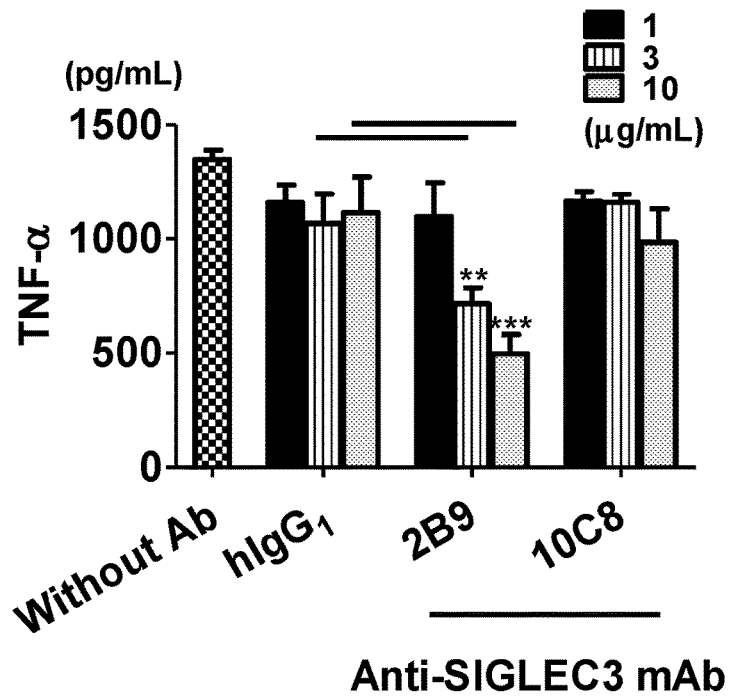

Clone 2B9 is apparently an agonistic mAb because it recruited SHP-1 and SHP-2 (FIG. 4, Panel A) and suppressed TNF-α production from Pam3csk4-stimulated moDC (FIG. 4, Panel B). Clones 3B8, 4D2 and 5E3 had similar features as clone 2B9, thus were also regarded as agonistic mAbs (data not shown). In contrast, clone 10C8 was unable to recruit SHP-1 and SHP-2 neither to suppress Pam3csk4-induced TNF-α production under the same condition (FIG. 4, Panels A and B), suggesting that clone 10C8 was unable to trigger inhibitory signal via Siglec-3.

Figure 5:
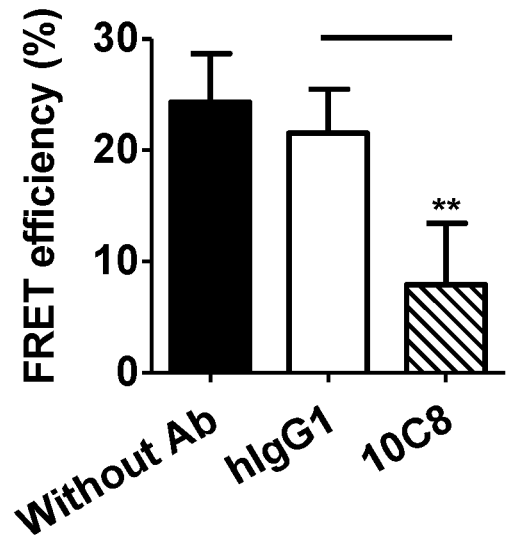
Figure 5:
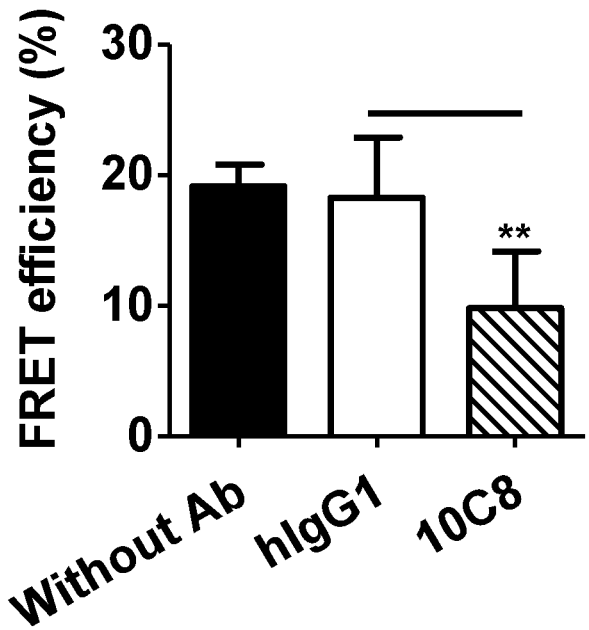

Moreover, clone 10C8 was able to inhibit Siglec-3 and HBV interaction in PBMC isolated from CHB patients as shown by fluorescence resonance energy transfer (FRET) assay (FIG. 5, Panel A). The fluorescence images indicated that Siglec-3 and HBV were colocalized in PBMC of CHB patients in the presence of isotype control mAb (IgG1) or absence of mAb, while clone 10C8 was capable of blocking Siglec-3 and HBV interaction (data not shown). Similar observation was observed in moDC incubated with exogenous hHBV (FIG. 5, Panel B).

These results demonstrated that clone 10C8 is an antagonistic anti-Siglec-3 mAb that is useful in blocking HBV-Siglec-3 interaction in cell surface.

5.2 Antagonistic Anti-Siglec-3 mAb Reversed HBV-Mediated Suppression on TLR Ligand-Induced Cytokine Production Whether clone 10C8 was able to reverse hHBV-mediated suppressive effect was examined in this example.

Figure 6:
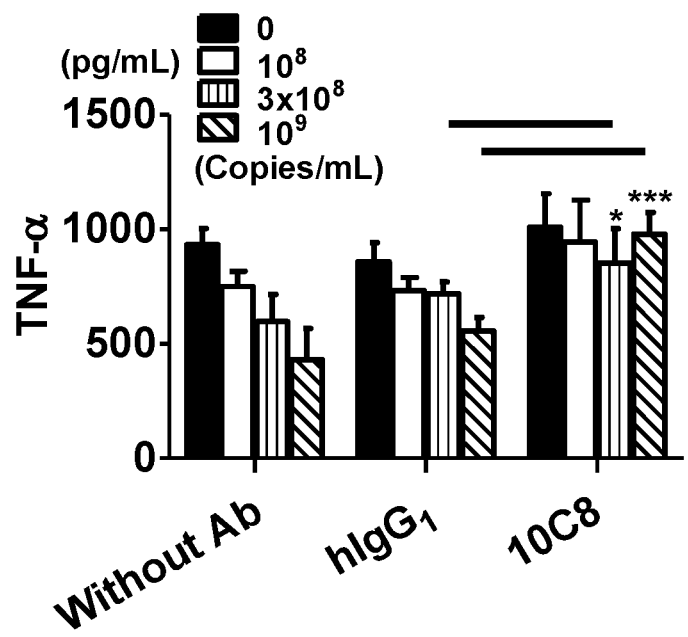
Figure 6:
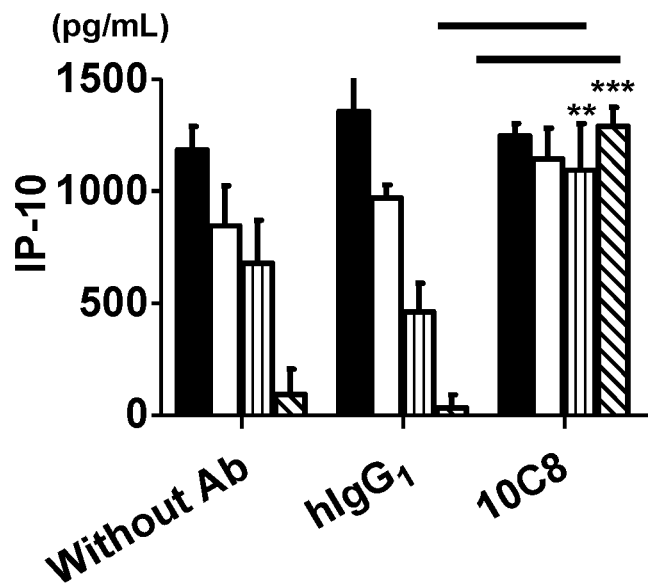
Figure 6:
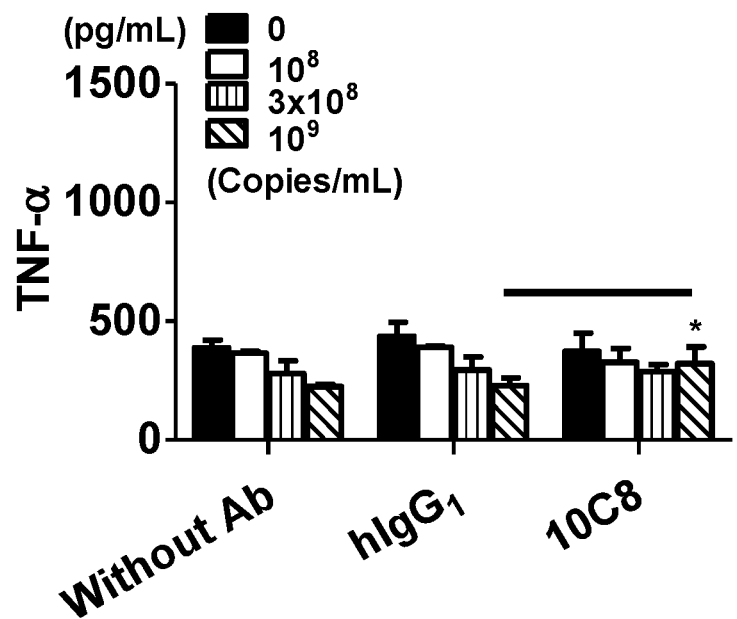
Figure 6:
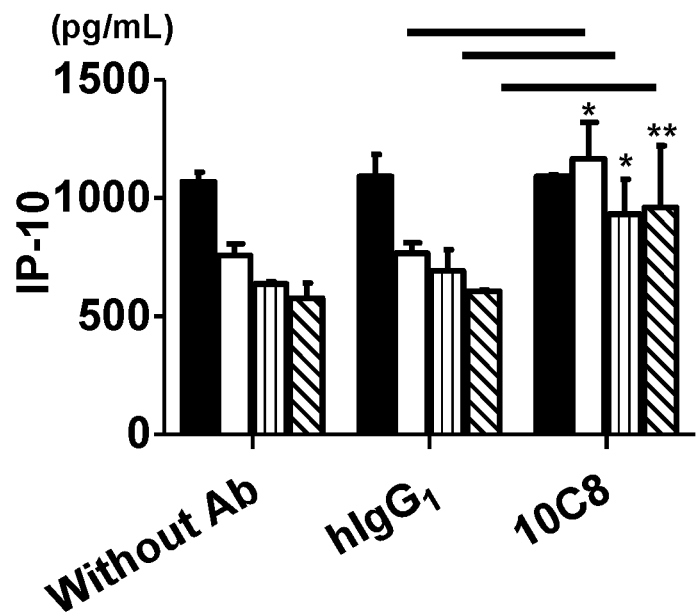
Figure 6:
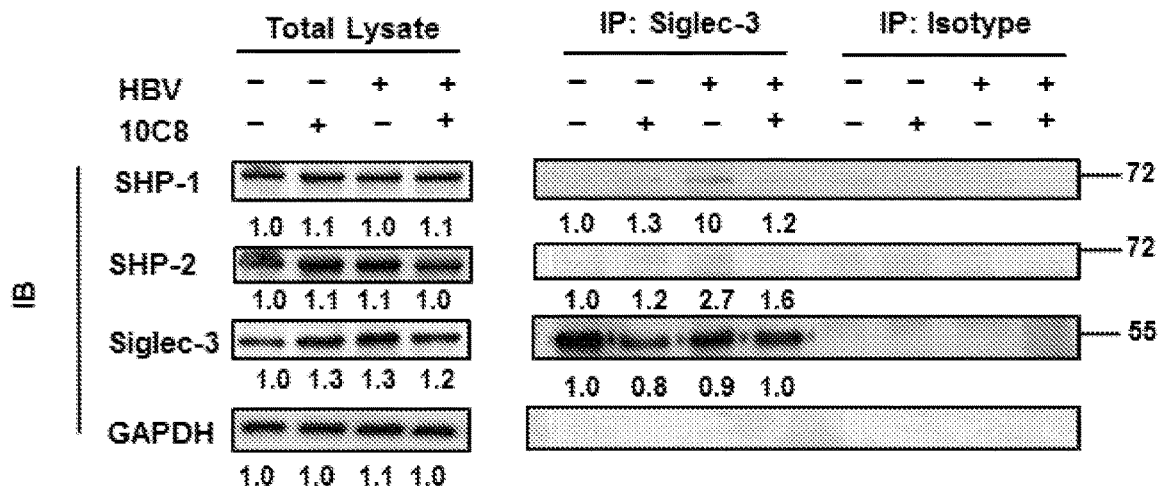
Figure 6:
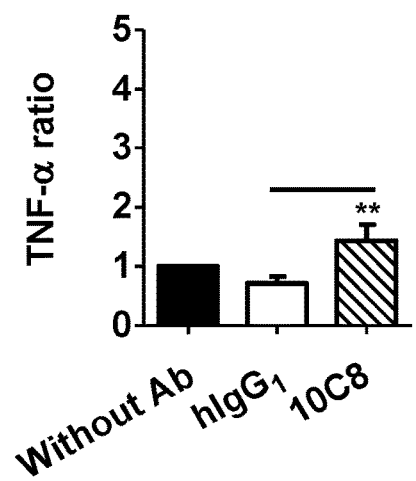
Figure 6:
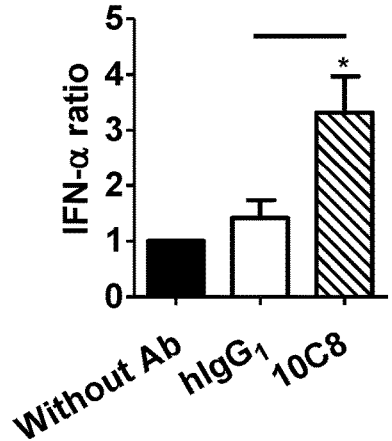
Figure 6:
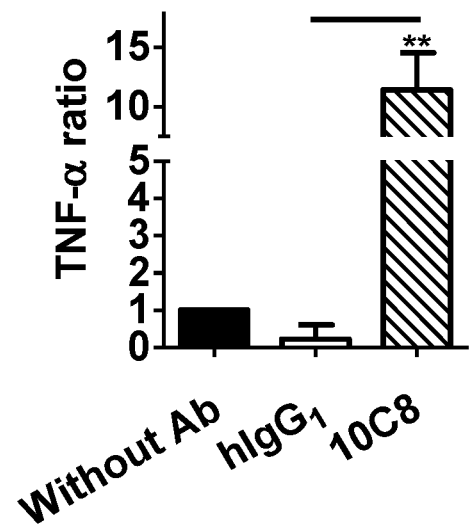
Figure 6:
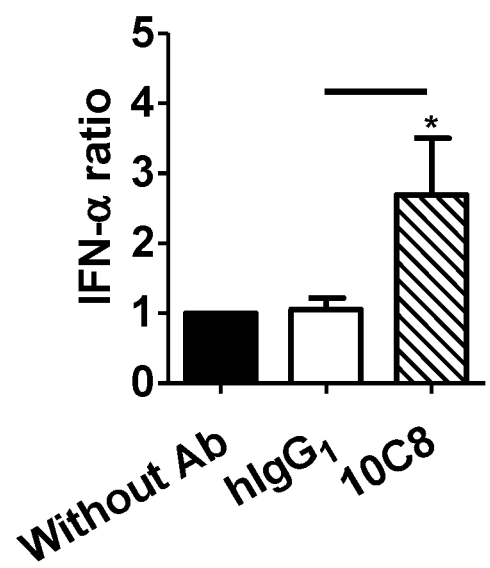

MoDC was incubated with pam3csk4 and poly (I:C)+ IFN-γ in the presence of hHBV, followed by detection of TNF-α and IP-10 by ELISA. The data of FIG. 6 indicated that TNF-α and IP-10 from Pam3sk4 or poly(I.C)+IFN-γ-stimulated moDC was suppressed by HBV in a dose-dependent manner, while clone 10C8 abolished the HBV-mediated suppressive effect (FIG. 6, Panels A to D). In addition, clone 10C8 also inhibited hHBV-induced SHP-1 and SHP-2 recruitment to Siglec-3 (FIG. 6, Panel E). Furthermore, clone 10C8 is able to enhance TNF-α and IFN-α production from TLR ligands-stimulated PBMC of CHB patients (FIG. 6, Panels F and I).

Accordingly, the data demonstrated that clone 10C8 was an antagonistic anti-Siglec-3 mAb, which may be useful in abolishing HBV-mediated inhibitory signals in moDCs.

In conclusion, the inventors of the present invention unexpectedly identify that HBV exhibits binding affinity to Siglec-3 receptors. Based on the finding, the present disclosure provides one novel anti-Siglec-3 mAb (i.e., 10C8 mAb), which is useful in reversing HBV-induced immunosuppression, and thus, may be further developed as medicaments for the treatment and/or prophylaxis of HBV infection.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An antibody or a fragment thereof for the prophylaxis or treatment of hepatitis B virus (HBV) infection, comprising,
 alight chain variable region comprising the amino acid sequences of VYY, ISSAG (SEQ ID NO: 3) and QYFNFP (SEQ ID NO: 4); and
 a heavy chain variable region comprising the amino acid sequences of NNGW (SEQ ID NO: 5), GIGPYGGSTF (SEQ ID NO: 6), and SRFIGSYSHM (SEQ ID NO: 7).

2. The antibody or a fragment thereof of claim 1, comprising an amino acid sequence at least 85% identical to SEQ ID NO: 8 and an amino acid sequence at least 85% identical to SEQ ID NO: 9.

3. The antibody or a fragment thereof of claim 2, wherein the antibody has the amino acid sequence of SEQ ID NO: 8 and the amino acid sequence of SEQ ID NO: 9.

4. A method of preventing or treating HBV infection in a subject, comprising administering to the subject an effective amount of the antibody or a fragment thereof of claim 1.

5. The method of claim 4, wherein the antibody comprises an acid sequence at least 85% identical to SEQ ID NO: 8 and an amino acid sequence at least 85% identical to SEQ ID NO: 9.

6. The method of claim 5, wherein the antibody has the amino acid sequence of SEQ ID NO: 8 and the amino acid sequence of SEQ ID NO: 9.

7. The method of claim 4, wherein the subject is a human.

8. A pharmaceutical composition for the prophylaxis or treatment of HBV infection, comprising an effective amount of the antibody or a fragment thereof of claim 1, and a pharmaceutically acceptable carrier.

9. The pharmaceutical composition of claim 8, wherein the antibody comprises an amino acid sequence at least 85% identical to SEQ ID NO: 8 and an amino acid sequence at least 85% identical to SEQ ID NO: 9.

10. The pharmaceutical composition of claim 9, wherein the antibody has the amino acid sequence of SEQ ID NO: 8 and the amino acid sequence of SEQ ID NO: 9.

* * * * *

SEQUENCE LISTING

```
<160> NUMBER OF SEQ ID NOS: 9

<210> SEQ ID NO 1
<211> LENGTH: 17
<212> TYPE: PRT
<213> ORGANISM: Artificial Sequence
<220> FEATURE:
<223> OTHER INFORMATION: synthesized-hHBsAg peptide 1

<400> SEQUENCE: 1
```

```
Thr Lys Pro Thr Asp Gly Asn Cys Thr Cys Ile Pro Ile Pro Ser Ser
1               5                   10                  15
Trp

<210> SEQ ID NO 2
<211> LENGTH: 19
<212> TYPE: PRT
<213> ORGANISM: Artificial Sequence
<220> FEATURE:
<223> OTHER INFORMATION: synthesized-hHBsAg peptide 2

<400> SEQUENCE: 2

Pro Ser Asp Gly Asn Cys Thr Cys Ile Pro Ile Pro Ser Ser Trp Ala
1               5                   10                  15
Phe Gly Lys

<210> SEQ ID NO 3
<211> LENGTH: 5
<212> TYPE: PRT
<213> ORGANISM: Artificial Sequence
<220> FEATURE:
<223> OTHER INFORMATION: synthesized-CDR-L2

<400> SEQUENCE: 3

Ile Ser Ser Ala Gly
1               5

<210> SEQ ID NO 4
<211> LENGTH: 6
<212> TYPE: PRT
<213> ORGANISM: Artificial Sequence
<220> FEATURE:
<223> OTHER INFORMATION: synthesized-CDR-L3

<400> SEQUENCE: 4

Gln Tyr Phe Asn Phe Pro
1               5

<210> SEQ ID NO 5
<211> LENGTH: 4
<212> TYPE: PRT
<213> ORGANISM: Artificial Sequence
<220> FEATURE:
<223> OTHER INFORMATION: synthesized-CDR-H1

<400> SEQUENCE: 5

Asn Asn Gly Trp
1

<210> SEQ ID NO 6
<211> LENGTH: 10
<212> TYPE: PRT
<213> ORGANISM: Artificial Sequence
<220> FEATURE:
<223> OTHER INFORMATION: synthesized-CDR-H2

<400> SEQUENCE: 6

Gly Ile Gly Pro Tyr Gly Gly Ser Thr Phe
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthesized-CDR-H3
```

```
<400> SEQUENCE: 7

Ser Arg Phe Ile Gly Ser Tyr Ser His Met
1               5                   10

<210> SEQ ID NO 8
<211> LENGTH: 237
<212> TYPE: PRT
<213> ORGANISM: Artificial Sequence
<220> FEATURE:
<223> OTHER INFORMATION: synthesized-VL region

<400> SEQUENCE: 8

Met Arg Val Pro Ala Gln Leu Leu Gly Leu Leu Leu Leu Trp Leu Pro
1               5                   10                  15

Gly Ala Arg Cys Asp Gly Thr Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Asp Val Tyr Tyr Val Ala Trp Tyr Gln Gln Lys Pro Gly
    50                  55                  60

Lys Ala Pro Lys Leu Leu Ile Ser Ser Ala Gly Gly Leu Tyr Ser Gly
65                  70                  75                  80

Val Pro Ser Arg Phe Ser Gly Ser Gly Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Tyr Phe Asn Phe Pro Leu Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 9
<211> LENGTH: 468
<212> TYPE: PRT
<213> ORGANISM: Artificial Sequence
<220> FEATURE:
<223> OTHER INFORMATION: synthesized-VH region

<400> SEQUENCE: 9

Met Gly Trp Ser Leu Ile Leu Leu Phe Leu Val Ala Val Ala Thr Arg
1               5                   10                  15

Val Ala Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Ile
        35                  40                  45
```

```
Asn Asn Gly Trp Ile His Trp Val Arg Gln Ala Pro Gly Lys Gly Leu
 50                  55                  60
Glu Trp Val Ala Gly Ile Gly Pro Tyr Gly Ser Thr Phe Tyr Ala
 65                  70                  75                  80
Asp Ser Val Lys Gly Arg Phe Thr Ile Ser Ala Asp Thr Ser Lys Asn
                     85                  90                  95
Thr Ala Tyr Leu Gln Met Asn Ser Leu Arg Ala Glu Asp Thr Ala Val
                100                 105                 110
Tyr Tyr Cys Ser Arg Phe Ile Gly Ser Tyr Ser His Met Asp Tyr Trp
                115                 120                 125
Gly Gln Gly Thr Leu Val Thr Val Ser Ser Ala Ser Thr Lys Gly Pro
                130                 135                 140
Ser Val Phe Pro Leu Ala Pro Ser Ser Lys Ser Thr Ser Gly Gly Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
                180                 185                 190
Ala Val Leu Gln Ser Ser Gly Leu Tyr Ser Leu Ser Ser Val Val Thr
                195                 200                 205
Val Pro Ser Ser Ser Leu Gly Thr Gln Thr Tyr Ile Cys Asn Val Asn
                210                 215                 220
His Lys Pro Ser Asn Thr Lys Val Asp Lys Lys Ala Glu Pro Lys Ser
225                 230                 235                 240
Cys Asp Lys Thr His Thr Cys Pro Pro Cys Pro Ala Pro Glu Leu Leu
                245                 250                 255
Gly Gly Pro Ser Val Phe Leu Phe Pro Pro Lys Pro Lys Asp Thr Leu
                260                 265                 270
Met Ile Ser Arg Thr Pro Glu Val Thr Cys Val Val Val Asp Val Ser
                275                 280                 285
His Glu Asp Pro Glu Val Lys Phe Asn Trp Tyr Val Asp Gly Val Glu
                290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Asp Tyr Lys Cys Lys Val Ser Asn Lys Ala Leu Pro Ala Pro
                340                 345                 350
Ile Glu Lys Thr Ile Ser Lys Ala Lys Gly Gln Pro Arg Glu Pro Gln
                355                 360                 365
Val Tyr Thr Leu Pro Pro Ser Arg Asp Glu Leu Thr Arg Asn Gln Val
                370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
                420                 425                 430
```

-continued

```
Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
        450                 455                 460

Ser Pro Gly Lys
465
```